US010960035B2

(12) United States Patent
Koltai et al.

(10) Patent No.: US 10,960,035 B2
(45) Date of Patent: Mar. 30, 2021

(54) ERODIUM CRASSIFOLIUM L'HER PLANT EXTRACTS AND USES THEREOF

(71) Applicants: The State of Israel, Ministry of Agriculture & Rural Development, Agricultural Research Organization (ARO) (Volcani Center), Rishon-LeZion (IL); The Economic Company For The Development Of Ramat Hanegev Ltd., Ramat HaNegev Regional Council (IL)

(72) Inventors: Hinanit Koltai, Rishon-LeZion (IL); Yoram Kapulnik, Karmey Yosef (IL); Marcelo Fridlender, Mazkeret Batia (IL); Einav Mayzlish Gati, Moshav Hemed (IL); Nasser Ahmed, Jerusalem (IL); Shemer Ben Zion, Moshav Kadesh Barnea (IL)

(73) Assignees: The State of Israel, Ministry of Agriculture & Rural Development, Agricultural Research Organization (ARO) (Voleaui Center), Rishon-LeZiou (IL); The Economic Company For The Development Of Ramat Hanegev Ltd., Ramat HaNegev (IL)

( * ) Notice: Subject to any disclaimer, the term of this patent is extended or adjusted under 35 U.S.C. 154(b) by 382 days.

(21) Appl. No.: 15/563,595

(22) PCT Filed: Mar. 31, 2016

(86) PCT No.: PCT/IL2016/050348
§ 371 (c)(1),
(2) Date: Oct. 1, 2017

(87) PCT Pub. No.: WO2016/157192
PCT Pub. Date: Oct. 6, 2016

(65) Prior Publication Data
US 2018/0092954 A1 Apr. 5, 2018

Related U.S. Application Data

(60) Provisional application No. 62/141,313, filed on Apr. 1, 2015.

(51) Int. Cl.
| | | |
|---|---|---|
| *A61K 36/185* | (2006.01) | |
| *A61Q 19/00* | (2006.01) | |
| *A23L 33/105* | (2016.01) | |
| *A61K 8/9789* | (2017.01) | |
| *A61K 8/96* | (2006.01) | |

(52) U.S. Cl.
CPC .......... *A61K 36/185* (2013.01); *A23L 33/105* (2016.08); *A61K 8/96* (2013.01); *A61K 8/9789* (2017.08); *A61Q 19/00* (2013.01); *A23V 2002/00* (2013.01); *A23V 2250/21* (2013.01); *A61K 2236/333* (2013.01); *A61K 2236/51* (2013.01)

(58) Field of Classification Search
None
See application file for complete search history.

(56) References Cited

U.S. PATENT DOCUMENTS

| | | |
|---|---|---|
| 6,410,588 B1 | 6/2002 | Feldmann et al. |
| 6,949,582 B1 | 9/2005 | Wallace |
| 8,980,942 B2 | 3/2015 | Stinchcomb et al. |
| 2002/0132021 A1 | 9/2002 | Raskin et al. |
| 2004/0175367 A1 | 9/2004 | Herlyn et al. |
| 2007/0032544 A1 | 2/2007 | Korthout et al. |
| 2009/0197941 A1 | 8/2009 | Guy et al. |
| 2010/0249223 A1 | 9/2010 | Di Marzo et al. |
| 2010/0286098 A1 | 11/2010 | Robson et al. |
| 2012/0128777 A1 | 5/2012 | Keck et al. |
| 2013/0059018 A1 | 3/2013 | Parolaro et al. |
| 2013/0122114 A1 | 5/2013 | Golan et al. |
| 2013/0224151 A1 | 8/2013 | Pearson et al. |
| 2014/0221469 A1 | 8/2014 | Ross et al. |
| 2015/0086653 A1 | 3/2015 | Parolaro et al. |
| 2015/0297654 A1 | 10/2015 | Speier |
| 2016/0106705 A1 | 4/2016 | Verzura et al. |
| 2017/0007540 A1 | 1/2017 | Gupta |

FOREIGN PATENT DOCUMENTS

| | | | |
|---|---|---|---|
| CN | 101524405 A | * | 9/2009 |
| CN | 101904881 A | * | 12/2010 |
| EP | 2298283 | | 3/2011 |
| GB | 2393721 | | 4/2004 |
| WO | WO 03/061563 | | 7/2003 |
| WO | WO 2009/004302 | | 1/2009 |
| WO | WO 2011/051947 | | 5/2011 |
| WO | WO 2014/159688 | | 10/2014 |
| WO | WO 2016/103254 | | 6/2016 |
| WO | WO 2016/157192 | | 10/2016 |

(Continued)

OTHER PUBLICATIONS

Gillet (J Natl Cancer Inst (2013), vol. 105, pp. 452-458).*
Hynds (Disease Models and Mechanisms (2018), vol. 11, p. 1-5).*
International Preliminary Report on Patentability dated Sep. 19, 2019 From the International Bureau of WIPO Re. Application No. PCT/ IL2018/050248. (10 Pages).
International Preliminary Report on Patentability dated Sep. 19, 2019 From the International Bureau of WIPO Re. Application No. PCT/IL2018/050249. (10 Pages).
International Search Report and the Written Opinion dated Jun. 7, 2018 From the International Searching Authority Re. Application No. PCT/ IL2018/050248. (17 Pages).
International Search Report and the Written Opinion dated Jun. 17, 2018 From the International Searching Authority Re. Application No. PCT/IL2018/050249. (15 Pages).

(Continued)

*Primary Examiner* — Susan Hoffman

(57) ABSTRACT

Polar extracts of *Erodium* plants are disclosed as well as pharmaceutical compositions and cosmetic compositions comprising same. Uses of the polar extracts are also disclosed.

4 Claims, 18 Drawing Sheets
(18 of 18 Drawing Sheet(s) Filed in Color)

(56) References Cited

FOREIGN PATENT DOCUMENTS

| WO | WO 2016/189525 | 12/2016 |
|---|---|---|
| WO | WO 2017/013661 | 1/2017 |
| WO | WO 2017/158609 | 9/2017 |
| WO | WO 2018/163163 | 9/2018 |
| WO | WO 2018/163164 | 9/2018 |

OTHER PUBLICATIONS

Supplementary European Search Report and the European Search Opinion dated Nov. 6, 2018 From the European Patent Office Re. Application No. 16771541.6. (8 Pages).

Perera et al. "Immunomodulatory Activity of a Chinese Herbal Drug Yi Shen Juan Bi in Adjuvant Arthritis", Indian Journal of Pharmacology, XP055517710, 42(2): 65-69, Apr. 2010.

Aizpurua-Olaizola et al. "Evolution of the Cannabinoid and Terpene Content During the Growth of *Cannabis sativa* Plants From Different Chemotypes", Journal of Natural Products, 79(2): 324-331, Feb. 2, 2016.

Aviello et al. "Chemopreventive Effect of the Non-Psychotropic Phytocannabinoid Cannabidiol on Experimental Colon Cancer", Journal of Molecular Medicine, 90(8): 925-934, Published Online Jan. 10, 2012.

Ben-Shabat et al. "An Entourage Effect: Inactive Endogenous Fatty Acid Glycerol Esters Enhance 2-Arachidonoyl-Glycerol Cannabinoid Activity", European Journal of Pharmacology, 353(1): 23-31, Jul. 17, 1998.

Borrelli et al. "Colon Carcinogenesis is Inhibited by the TRPM8 Antagonist Cannabigerol, A Cannabis-Derived Non-Psychotropic Cannabinoid", Carcinogenesis, 35(12): 2787-2797, Advance Access Publication Sep. 30, 2014.

D'Haens et al. "Future Directions in Inflammatory Bowel Disease Management", Journal of Crohn's and Colitis, 8(8): 726-734, Aug. 2014.

ElSohly et al. "Phytochemistry of *Cannabis sativa* L.", Progress in the Chemistry of Organic Natural Products: Phytocannabinoids, POGRCHEM, 103: 1-36, Published Online Jan. 25, 2017.

Greenhough et al. "The Cannabinoid [Delta]9-Tetrahydrocannabinol Inhibits RAS-MAPK and P13K-AKT Survival and Signalling and Induces BAD-Mediated Apoptosis in Colorectal Cancer Cells", International Journal of Cancer, 121(10): 2172-2180, Published Online Jun. 21, 2007.

Greineisen et al. "Immunoactive Effects of Cannabinoids: Considerations for the Therapeutic Use of Cannabinoid Receptor Agonists and Antagonists", International Immunopharmacology, 10(5): 547-555, May 2010.

Hill et al. "Cannabidivarin-Rich Cannabis Extracts are Anticonvulsant in Mouse and Rat via a CB1 Receptor-Independent Mechanism", British Journal of Pharmacology, 170(3): 679-692, Oct. 2013.

Ihenetu et al. "Inhibition of Interleukin-8 Release in the Human Colonic Epithelial Cell Line HT-29 by Cannabinoids", European Journal of Pharmacology, 458(1-2): 207-215, Jan. 2003.

Izzo et al. "Cannabinoids is an Intestinal Inflammation and Cancer", Pharmacological Research, 60(2): 117-125, Aug. 2009.

Javid et al. "Cannabinoid Pharmacology in Cancer Research: A New Hope for Cancer Patients?", European Journal of Pharmacology, 775: 1-4, Mar. 15, 2016.

Mechoulam et al. "Cannabidiol: An Overview of Some Pharmacological Aspects", The Journal of Clinical Pharmacology, 42(S1): 11S-19S, Nov. 2002.

Mechoulam et al. "Chemical Basis of Hashish Activity", Science, 169(3945): 611-612, Aug. 7, 1970.

Mechoulam et al. "Hashish—IV: The Isolation and Structure of Cannabinolic Cannabidiolic and Cannabigerolic Acids", Tetrahedron, 21(5): 1223-1229, Jan. 1965.

Naftali et al. "Cannabis Induces a Clinical Response in Patients With Crohn's Disease: A Prospective Placebo-Controlled Study", Clinical Gastroenterology and Hepatology, 11(10): 1276-1280, Oct. 2013.

Naftali et al. "Treatment of Crohn's Disease With Cannabis: An Observational Study", The Israel Medical Association Journal, IMAJ, 13(8): 455-458, Aug. 2011.

Pagano et al. "An Orally Active Cannabis Extract With High Content in Cannabidiol Attenuates Chemically-Induced Intestinal Inflammation and Hypermotility in the Mouse", Frontiers in Pharmacology, 7(Art.341): 1-12, Oct. 4, 2016.

Romano et al. "Inhibition of Colon Carcinogenesis by a Standarized *Cannabis sativa* Extract With High Content of Cannabidiol", Phytomedicine, 21(5): 631-639, Apr. 15, 2014.

Romano et al. "Pure [Delta]9-Tetrahydrocannabivarin and a *Cannabis sativa* Extract With High Content in [Delta]9-Tetrahydrocannabivarin Inhibit Nitrite Production in Murine Peritoneal Macrophages", Pharmacological Research, 113: 199-208, Available Online Aug. 3, 2016.

Russo et al. "Taming THC: Potential Cannabis Synergy and Phytocannabinoid-Terpenoid Entourage Effects", British Journal of Pharmacology, 163(7): 1344-1364, Aug. 2011.

Ryberg et al. "The Orphan Receptor GPR55 is a Novel Cannabinoid Receptor", British Journal of Pharmacology, 152(7): 1092-1101, Published Online Sep. 17, 2007.

Sartor "Mechanisms of Disease: Pathogenesis of Crohn's Disease and Ulcerative Colitis", Nature Clinical Practice Gastroenterology & Hepatology, 3(7): 390-407, Jul. 2006.

Schicho et al. "Cannabis Finds Its Way Into Treatment of Crohn's Disease", Pharmacology, 93(1-2): 1-3, Published Online Dec. 17, 2013.

Stancic et al. "The GPR55 Antagonist CID16020046 Protects Against Intestinal Inflammation", Neurogastroenterology & Motility, 27(10): 1432-1445, Oct. 2015.

Storr et al. "Activation of the Cannabinoid 2 Receptor (CB2) Protects Against Experimental Colitis", Inflammation Bowel Disease, 15(11): 1678-1685, Published Online Apr. 30, 2009.

Sturm et al. "Epithelial Restitution and Wound Healing in Inflammatory Bowel Disease", World Journal of Gastroenterology, 14(3): 348-353, Jan. 21, 2008.

Wright et al. "Cannabinoid CB2 Receptors in the Gastrointestinal Tract: A Regulatory System in States of Inflammation", British Journal of Pharmacology, 153(2): 263-270, Published Online Oct. 1, 2007.

International Preliminary Report on Patentability dated Nov. 9, 2017 From the International Bureau of WIPO Re. Application No. PCT/IL2016/050348. (8 Pages) Correction.

International Preliminary Report on Patentability dated Oct. 12, 2017 From the International Bureau of WIPO Re. Application No. PCT/IL2016/050348. (8 Pages).

International Search Report and the Written Opinion dated Jul. 7, 2016 From the International Searching Authority Re. Application No. PCT/IL2016/050348.

International Search Report and the Written Opinion dated Jun. 26, 2017 From the International Searching Authority Re. Application No. PCT/IL2017/050338. (10 Pages).

Colbert "Cannabinoid Profile: Tetrahydrocannabinolic Acid (THCa)", TheLeafOnline, 5 P., Jul. 15, 2014.

Danin "Erodium Crassifolium, Erodium Hirtum, Hoary-Leaved Heron's-Bill", Flowers of Israel, Retrieved From the Internet, p. 1-3, Aug. 8, 2014.

De Filippis et al. "Cannabidiol Reduces Intestinal Inflammation Through the Control of Neuroimmune Axis", PLoS ONE, 6(12): e28159-1-e28159-9, Dec. 6, 2011. Figs.5-8.

De Graaf et al. "Preparation and Incubation of Precision-Cut Liver and Intestinal Slices for Application in Drug Metabolism and Toxicity Studies", Nature Protocols, 5(9): 1540-1551, Published Online Aug. 19, 2010.

De Kanter et al. "Precision-Cut Organ Slices as a Tool to Study Toxicity and Metabolism of Xenobiotics With Special Reference to Non-Hepatic Tissues", Current Drug Metabolism, 3(1): 39-59, Feb. 2002.

Evans et al. "The Development of a Method for the Preparation of Rat Intestinal Epithelial Cell Primary Cultures", Journal of Cell Science, 101: 219-231, Jan. 31, 1992. Abstract, Figs.1, 2, Table 1, p. 222, Left col., Para 5, p. 228, Left col., 1st Para.

(56) References Cited

OTHER PUBLICATIONS

Gohar et al. "Antibacterial Polyphenol From Erodium Glaucophyllum", Zeitung fuer Naturforschung, 58(9-10): 670-674, Sep.-Oct. 2003. p. 670, 672-673.

Harvey et al. "Interleukin 17A Evoked Mucosal Damage is Attenuated by Cannabidiol and Anandamide in a Human Colonic Explant Model", Cytokine, 65(2): 236-244, Available Online Nov. 13, 2013. p. 239, Left col., 1st Para, p. 243, Left col., 3rd Para, Figs.1, 2.

MatTek Corporation "EpiIntestinal™", Overiew, MatTek Corporation, 8 P., 2017.

Sato et al. "Long-Term Expansion of Epithelial Organoids From Human Colon, Adenoma, Adenocarcinoma, and Barrett's Epithelium", Gastroenterology, 141: 1762-1772, Sep. 2, 2011. p. 1763, Left col., 5th Para, Right col., Para 1-2, p. 1764, Right col., 3rd Para, p. 1765, Left col., 2nd Para, Fig.1.

Sroka et al. "Antioxidative Effect of Extracts From *Erodium cicutarium* L.", Zeitung fuer Naturforschung, 49(11-12): 881-884, Nov.-Dec. 1994.

International Preliminary Report on Patentability dated Sep. 27, 2018 From the International Bureau of WIPO Re. Application No. PCT/IL2017/050338. (7 Pages).

Communication Pursuant to Article 94(3) EPC dated Jan. 29, 2020 From the European Patent Office Re. Application No. 16771541.6. (5 Pages).

Office Action dated Jan. 20, 2020 From the Israel Patent Office Re. Application No. 254823 and Its Translation Into English. (5 Pages).

\* cited by examiner

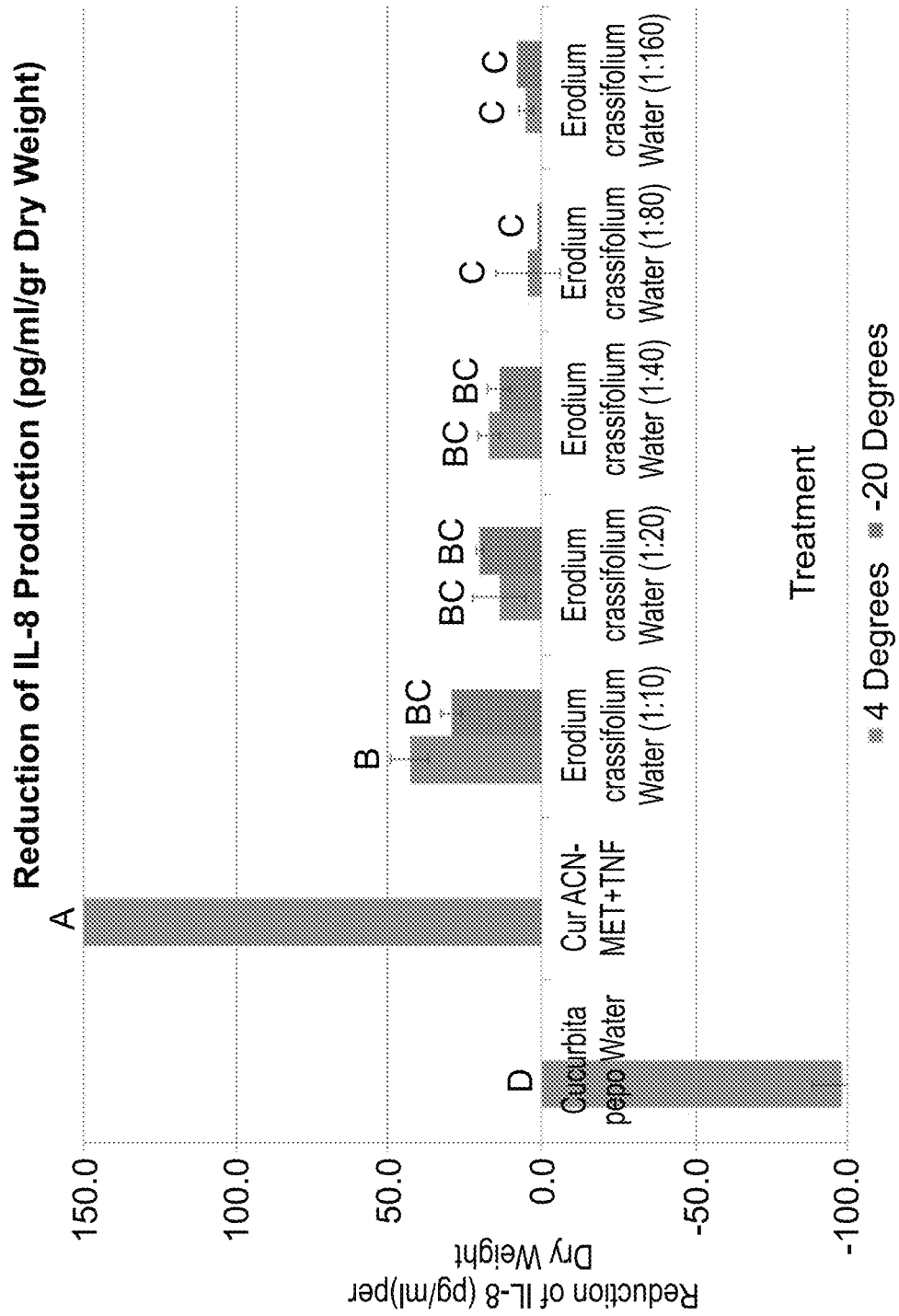

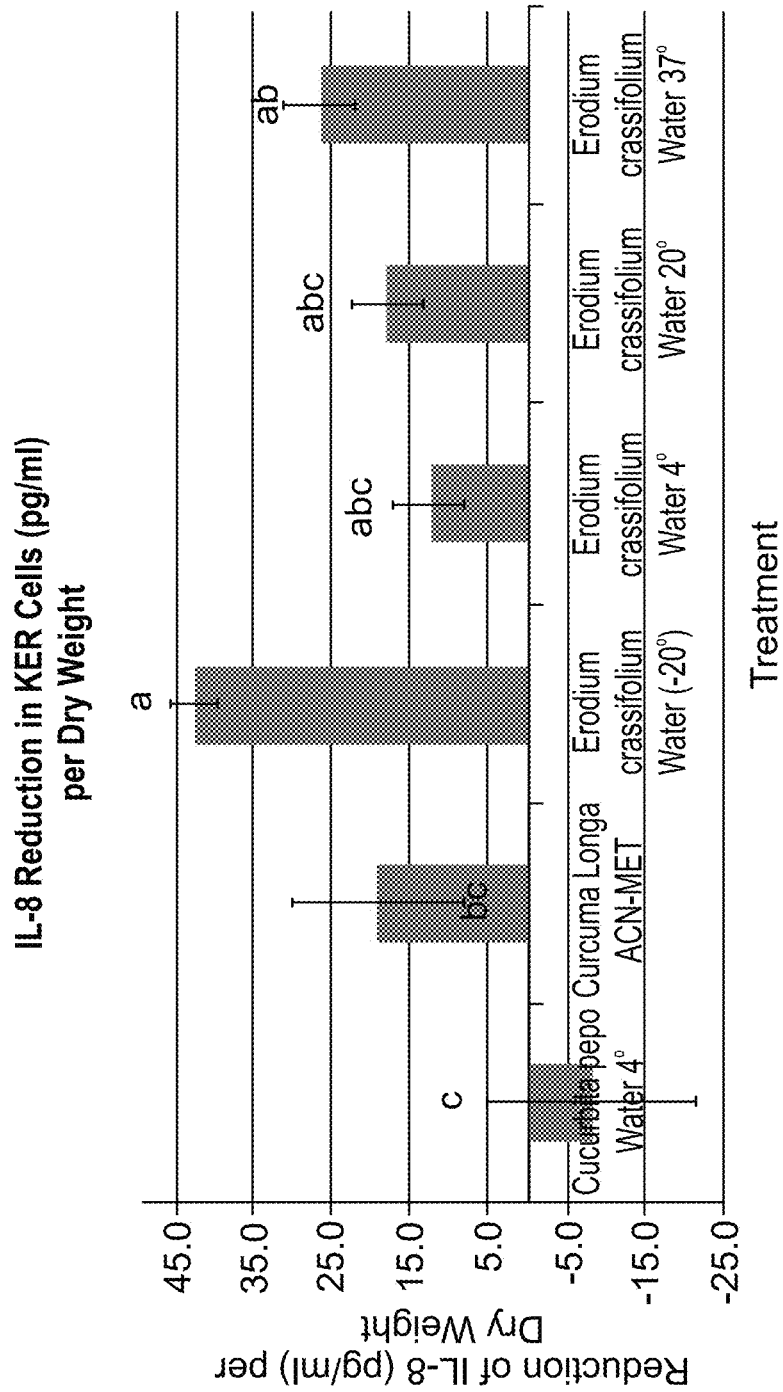

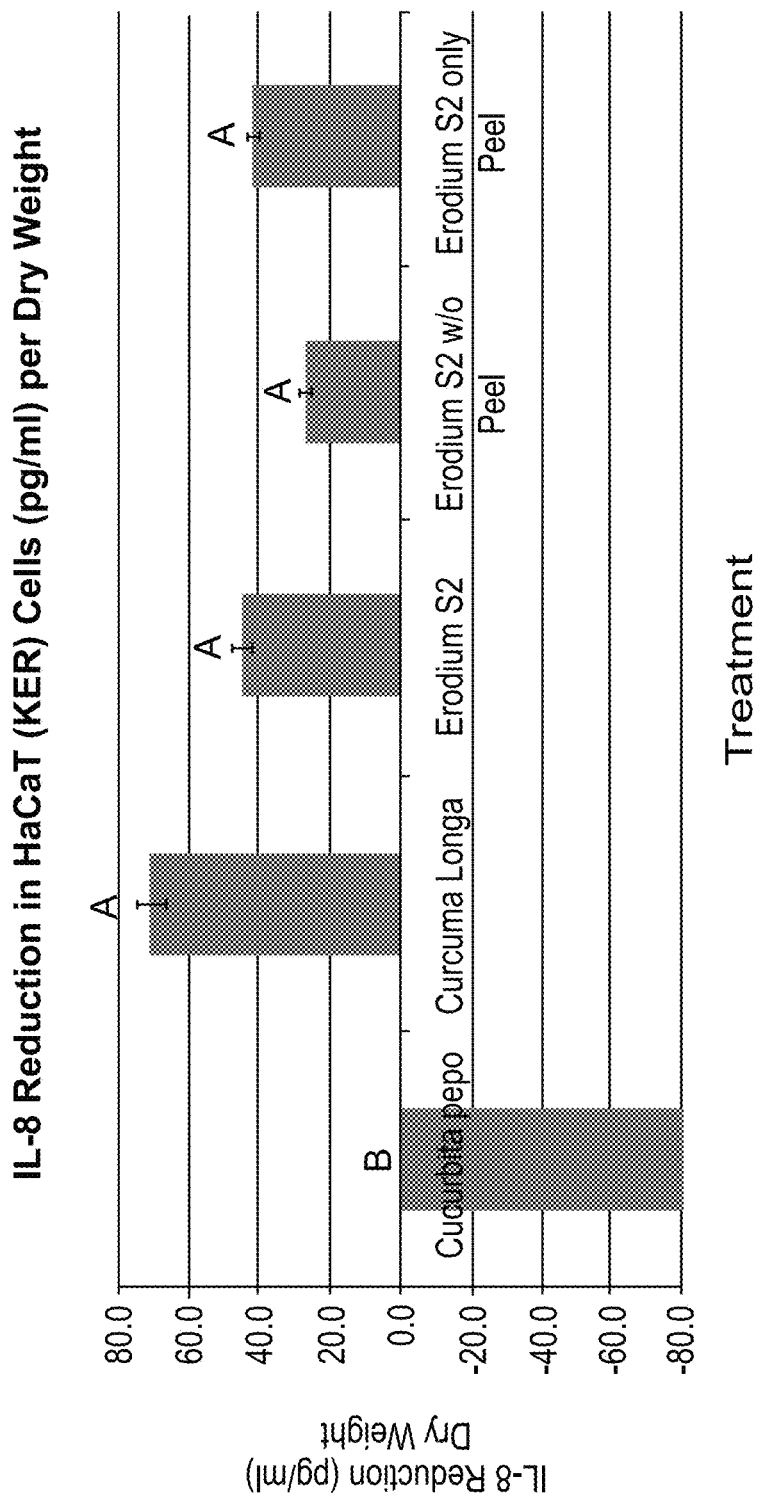

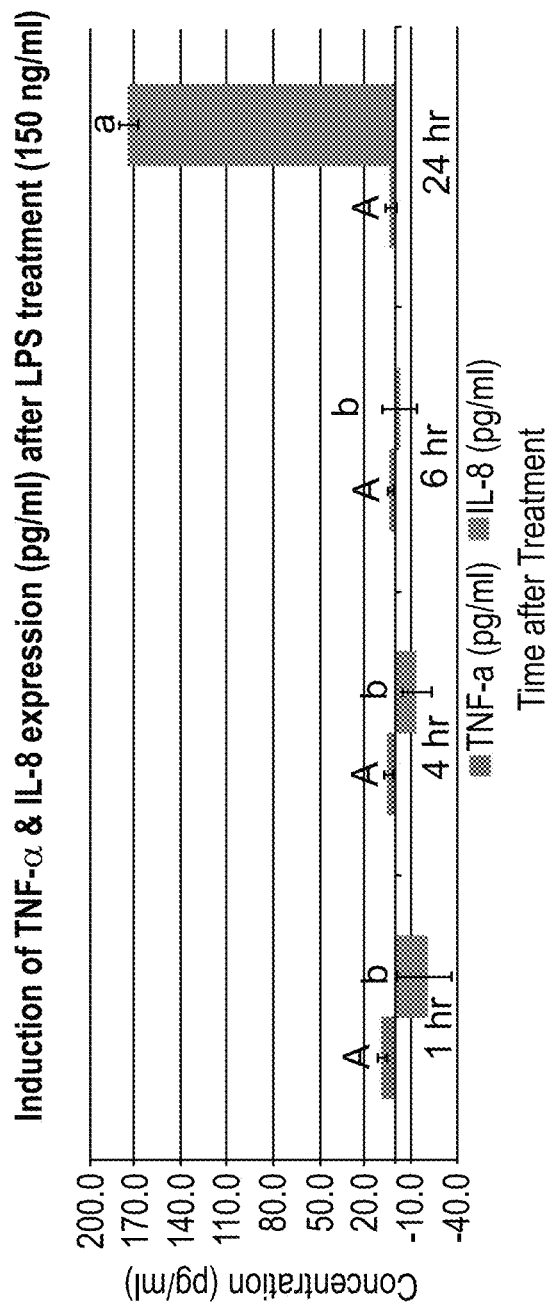
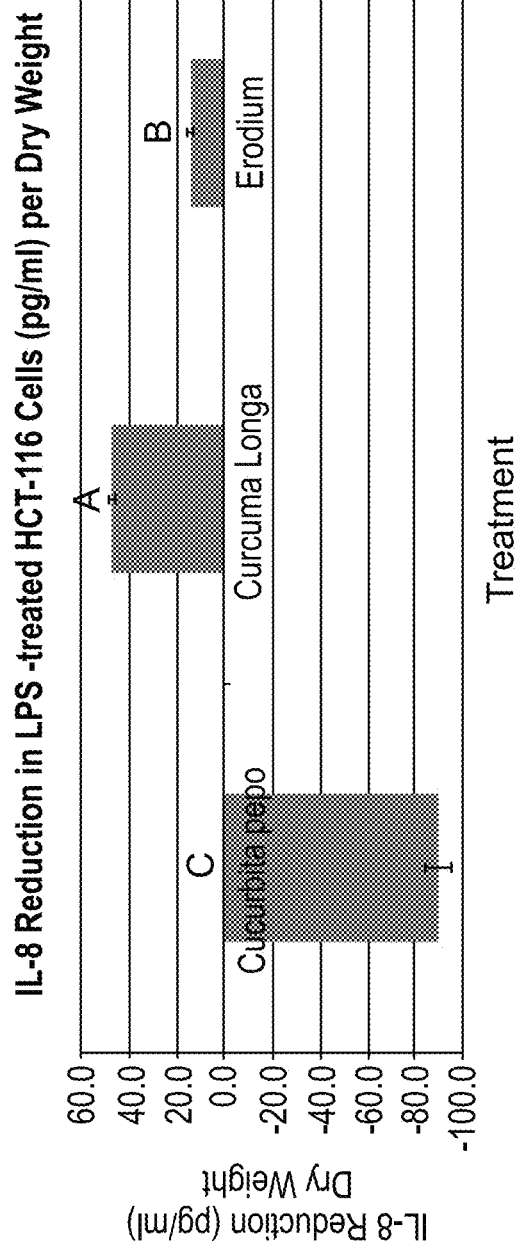
FIG. 12A
FIG. 12B

*ERODIUM CRASSIFOLIUM* L'HER PLANT EXTRACTS AND USES THEREOF

RELATED APPLICATIONS

This application is a National Phase of PCT Patent Application No. PCT/IL2016/050348 having International filing date of Mar. 31, 2016, which claims the benefit of priority under 35 USC § 119(e) of U.S. Provisional Patent Application No. 62/141,313 filed on Apr. 1, 2015. The contents of the above applications are all incorporated by reference as if fully set forth herein in their entirety.

FIELD AND BACKGROUND OF THE INVENTION

The present invention, in some embodiments thereof, relates to extracts of *Erodium* plants and, more particularly, but not exclusively, to polar extracts of tubers of *Erodium* plants.

*Erodium crassifolium* L'Her (Hairy storks bill), a member of the Geraniaceae family, is a hemicryptophyte (i.e. buds at or near the soil surface). It develops tubers on its roots. It has a suffruticose branching stem and flowering branches which are erect, slender, reddish brown, and thickly clothed with unequal villous hairs. Its leaves are alternate, rosette, pinnated or deeply lacinated. The flowers of this plant are hermaphrodite; pink and violet. The plant habitat is shrubsteppes and desert (FIGS. 1A-B). *Erodium crassifolium* L'Her is common in the Negev Highlands of Israel, with less than 90 mm annual precipitation. The plant produces a small tuber in the ground about 20 cm deep. This organ serves as a water and nutrient reservoir enabling the plant to overcome the dry season (FIGS. 1A-B). It is traditionally known that the tubers are edible, used mainly by the Bedouin nomadic tribes. The tubers are sweet in taste and best eaten in the late winter spring when they are whitish. They are typically eaten raw.

SUMMARY OF THE INVENTION

According to an aspect of some embodiments of the present invention there is provided a pharmaceutical composition comprising as the active ingredient an extract of tubers of an *Erodium* plant and a pharmaceutically acceptable carrier.

According to an aspect of some embodiments of the present invention there is provided a pharmaceutical composition comprising as the active ingredient an extract of an *Erodium crassifolium* L'Her plant and a pharmaceutically acceptable carrier.

According to an aspect of some embodiments of the present invention there is provided a polar extract of *Erodium* plant tubers, wherein the extract does not comprise plant tissue.

According to an aspect of some embodiments of the present invention there is provided a polar extract of *Erodium* plant tubers, wherein the extract has not been boiled.

According to an aspect of some embodiments of the present invention there is provided a composition of matter comprising a polar extract of *Erodium* plant tubers, the composition being dried.

According to an aspect of some embodiments of the present invention there is provided a food or feed comprising the polar extract or composition of matter of the present invention.

According to an aspect of some embodiments of the present invention there is provided a cosmetic composition comprising an extract of tubers of an *Erodium* plant.

According to an aspect of some embodiments of the present invention there is provided a method of generating a polar extract of an *Erodium* plant tubers comprising:

(a) contacting the tubers with a polar solvent under conditions to allow extraction of soluble agents from the tubers into the solvent to generate an extract; and (b) isolating the extract from the tubers, thereby generating the polar extract.

According to an aspect of some embodiments of the present invention there is provided a method of treating an inflammatory disease or a disease related to oxidative stress in a subject in need thereof comprising administering to the subject a therapeutically effective amount of a polar extract of tubers of an *Erodium* plant, thereby treating the disease.

According to an aspect of some embodiments of the present invention there is provided a method of performing a cosmetic care in a subject comprising applying to the skin of the subject a therapeutically effective amount of a polar extract of tubers of an *Erodium* plant, thereby performing the cosmetic care.

According to some embodiments of the present invention the *Erodium* plant is *Erodium crassifolium* L'Her.

According to some embodiments of the present invention the extract is generated from tubers or leaves of the *Erodium crassifolium* L'Her.

According to some embodiments of the present invention the extract is a polar extract.

According to some embodiments of the present invention the polar extract is a water extract.

According to some embodiments of the present invention the polar extract is an ethanol extract or Acetonitrile:Methanol extract.

According to some embodiments of the present invention the extract does not comprise material from more than two plants of different species.

According to some embodiments of the present invention the food is a food additive.

According to some embodiments of the present invention the extract is a polar extract.

According to some embodiments of the present invention the polar solvent is selected from the group consisting of water, ethanol and Acetonitrile:Methanol.

According to some embodiments of the present invention the method further comprises drying the extract following the contacting so as to generate a dried polar extract.

According to some embodiments of the present invention the method further comprises freezing the extract following the contacting so as to generate a frozen polar extract.

According to some embodiments of the present invention the method further comprises freezing the dried polar extract following the drying.

According to some embodiments of the present invention the pharmaceutical composition is formulated as a cream, an ointment, a gel, a tablet or a drop.

According to some embodiments of the present invention the cosmetic composition is formulated as a cream, a face mask, a scrub, a soap, a wash or a gel.

According to some embodiments of the present invention the disease related to oxidative stress is selected from the group consisting of rheumatoid arthritis, asthma, cancer, macular degeneration, inflammatory Bowel Disease (IBD), neurodegenerative diseases such as Parkinson's and Alzheimer diseases, arthritis, diabetes mellitus, atherosclerosis and chronic fatigue syndrome.

According to some embodiments of the present invention the disease is not epilepsy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B:
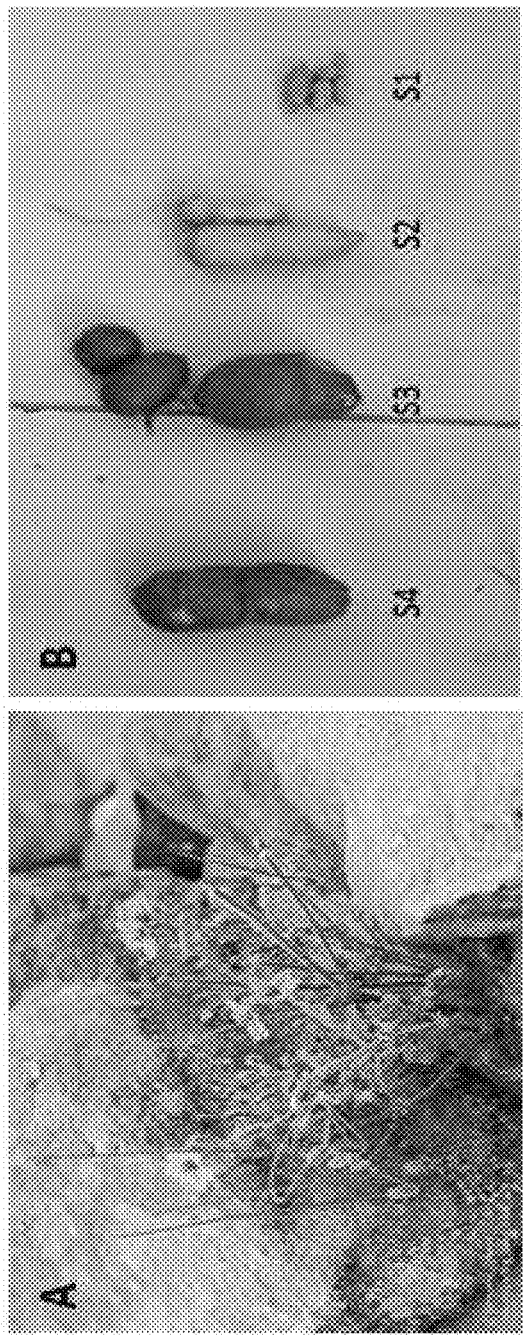

FIGS. 1A-B are photographs of *Erodium crassifolium* L'Her. (A) a desert shrub. (B) Different stages of tubers. S1—younger tubers; S4 older ones.

Figure 2A:
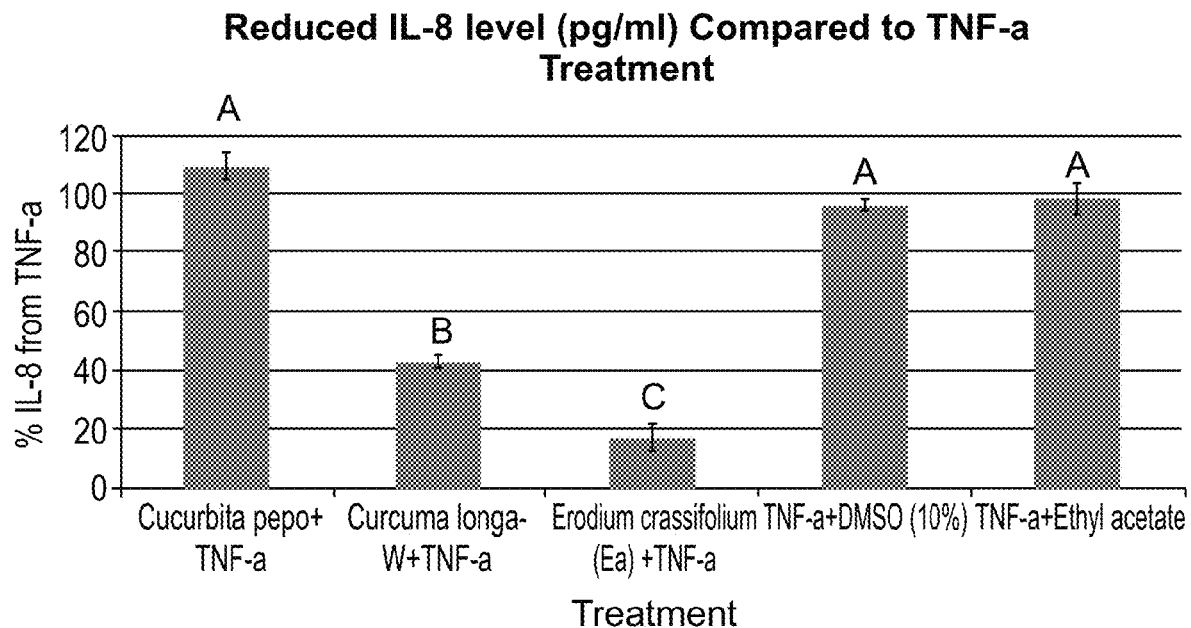
Figure 2B:
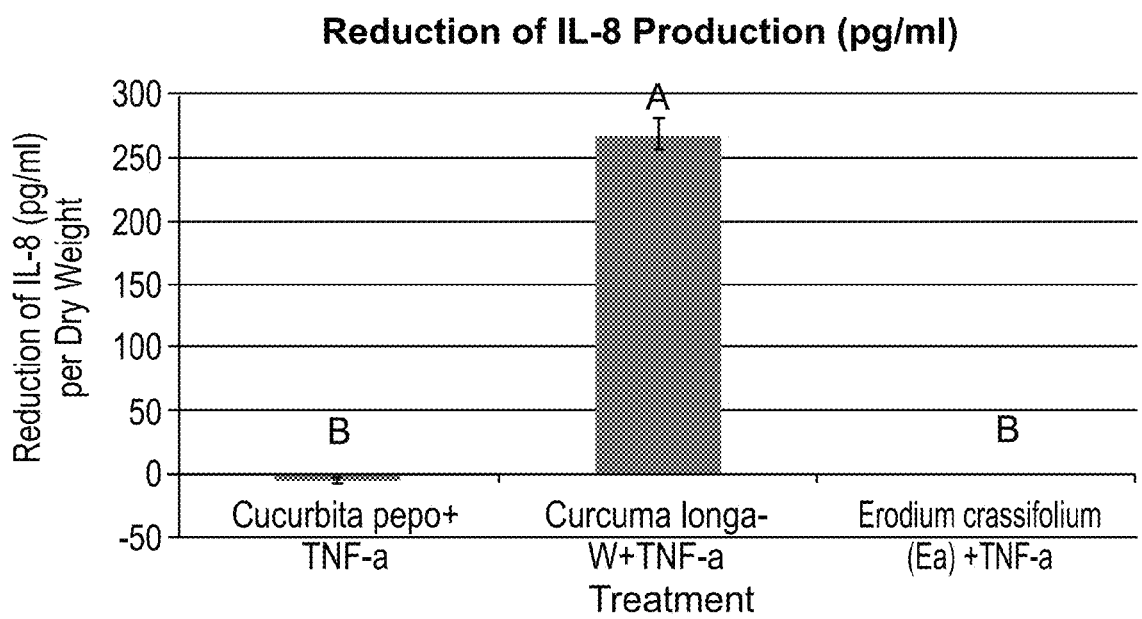

FIGS. 2A-B illustrate that *Erodium crassifolium* extracts comprise anti-inflammatory activity. (A) Reduced IL-8 level compared to TNF-α treatment. The level of IL-8 for each sample was calculated based on the obtained standard curve. The percentage of IL-8 level in relation to the control treatment (TNF-α) was calculated. (B) Anti-inflammatory specific activity (pg/ml per 1 gr dry weight). Calculation was performed by dividing the activity obtained in (A) by the dried weight. Means of replicates were subjected to statistical analysis by multiple comparison Tukey-Kramer test (P≤0.05). Levels not connected by same letter are significantly different. Ea=Ethyl acetate; W=Water (10% DMSO); *Cucurbita pepo*—extraction in Ea.

Figure 3A:
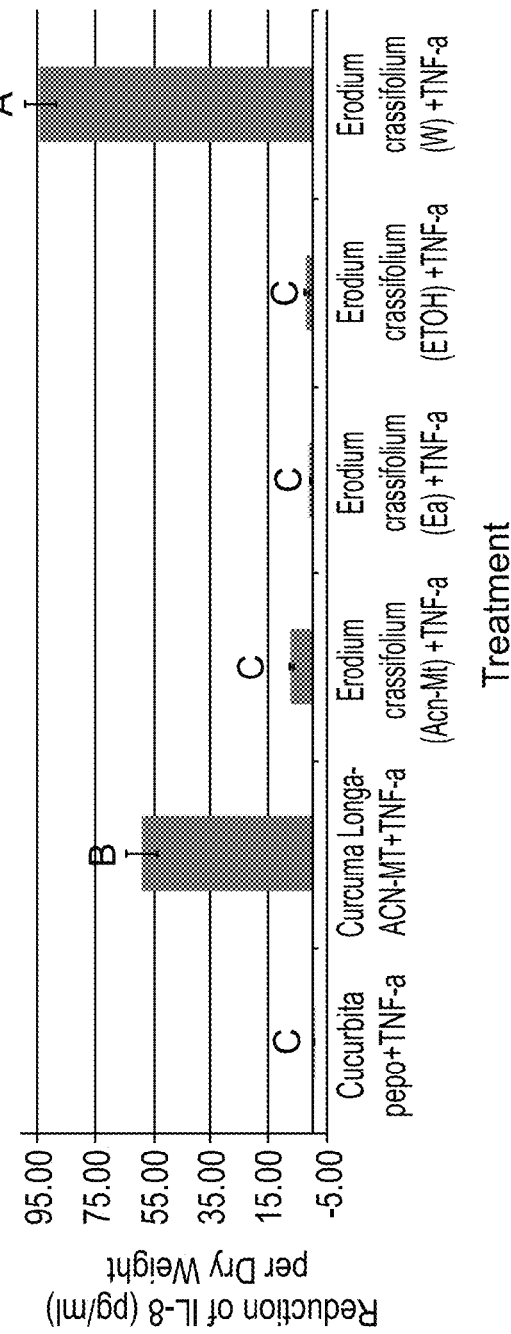
Figure 3B:
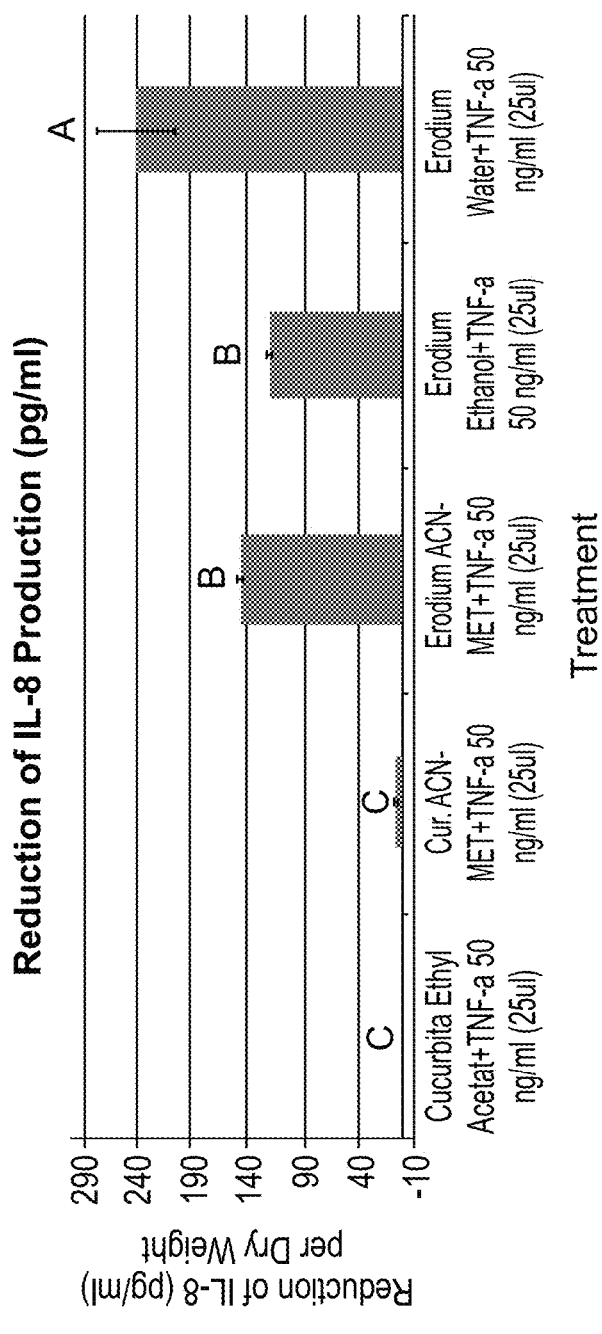

FIGS. 3A-B are graphs illustrating the anti-inflammatory activity in different *Erodium crassifolium* extracts. (A) Reduced IL-8 level in HCT-116 colon cells. (B) Reduced IL-8 level in BJ-hTERT skin cells. Anti-inflammatory specific activity (pg/ml per 1 gr dry weight) was calculated as previously described. Means of replicates statistically analyzed by multiple comparison Tukey-Kramer test (P≤0.05). Levels not connected by same letter are significantly different. Ea=Ethyl acetate; W=Water; ACN-MET=Acetonitrile-Methanol (1:1); ETOH=ethanol.

Figures 4A, 4B, 4C:
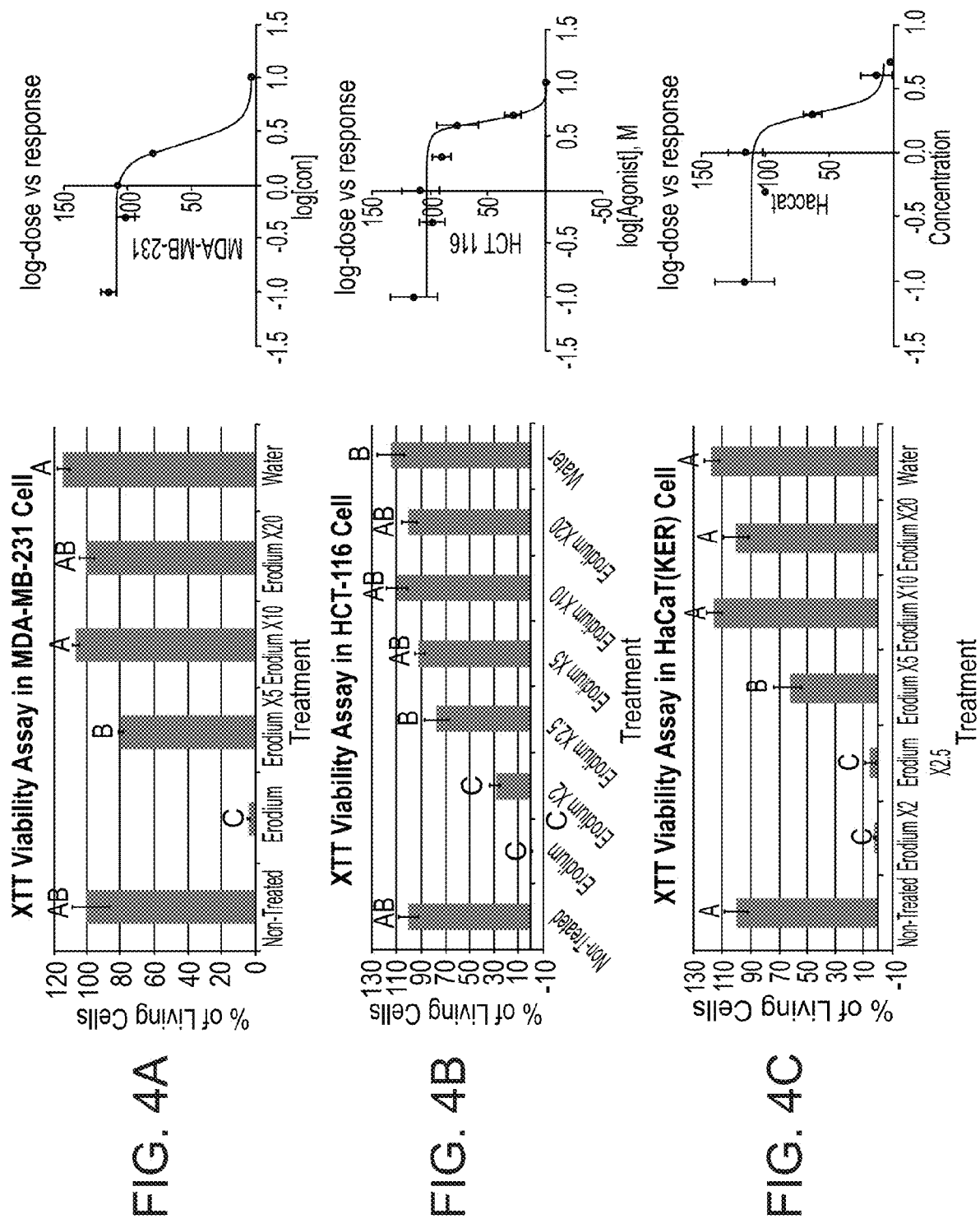

FIGS. 4A-C are dose response curves of MDA-MB-231, HCT-116 and HaCaT (KER) exposed to different concentrations of *E. crassifolium* extracts. (A) Viability assay using MDA-MB-231 cells. On the left XXT results and on the right log-dose vs. response curve from which $IC_{50}$ was calculated. $IC_{50}$=7.438. (B) Viability assay using HCT-116 cells. $IC_{50}$=13.55 (C) Viability assay using HaCaT (KER) cells. $IC_{50}$=6.132. *Erodium*=Non-diluted extract while *Erodium* ×2, ×2.5, ×5, ×10 and ×20 are extracts diluted 2, 2.5. 5, 10 or 20 times.

FIG. 5 is a graph illustrating the stability and dilution of *Erodium* extracts. Extracts were stored at either 4° C. or −20° C. for two weeks. The extracts were spun and filtered and stored at 4° C. until used. The ratios 1:10, 1:20, 1:40, 1:80 and 1:160 represent *Erodium* dilutions with water. Levels not connected by same letter are significantly different. ACN-MET=Acetonitrile-Methanol (1:1).

FIG. 6 is a graph illustrating the stability of *Erodium* extracts at different temperatures. Extracts were stored at (−20° C.), 4° C., 20° C. and 37° C. for a period 5 days before using for anti-inflammation assay in HaCaT skin cells. Levels not connected by same letter are significantly different. ACN-MET=Acetonitrile-Methanol (1:1).

Figure 7A:
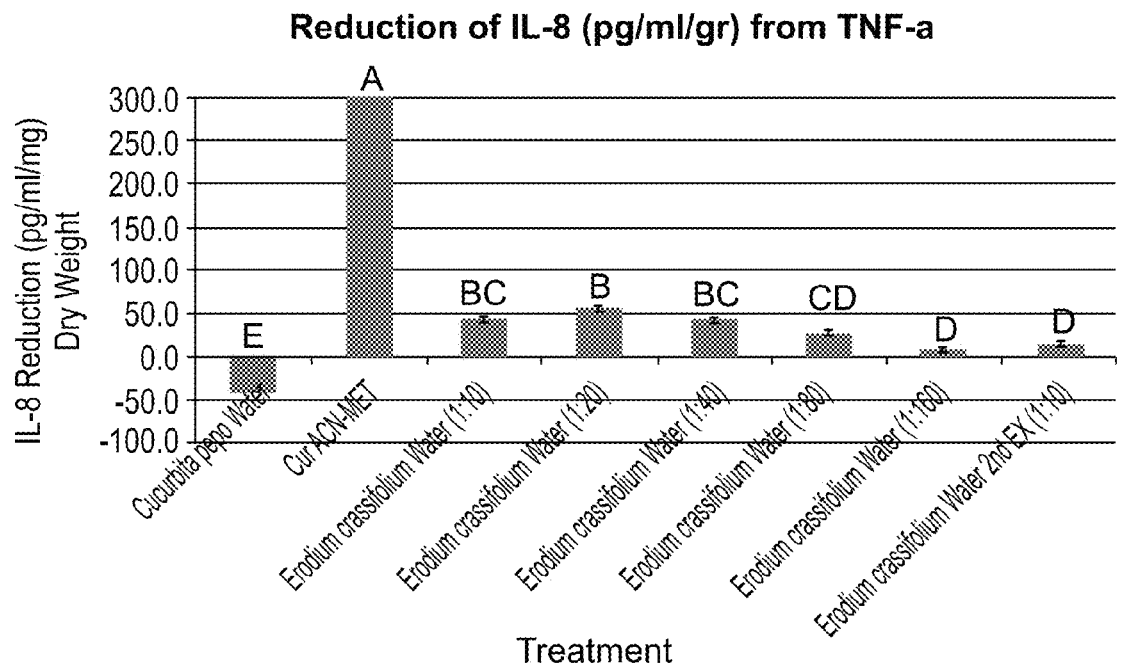
Figure 7B:
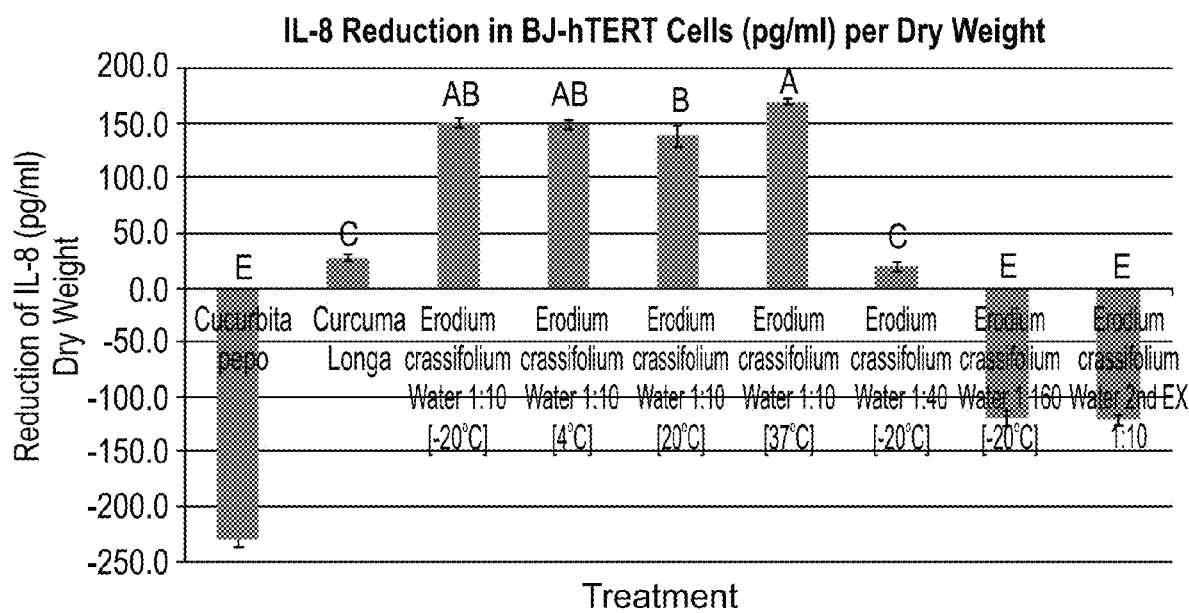

FIGS. 7A-B are graphs illustrating the anti-inflammatory activity of diluted *Erodium* extracts. (A) IL-8 ELISA assay in HCT-116 colon cells. (B) IL-8 ELISA assay using BJ-hTERT skin cells. The ratios 1:10, 1:20, 1:40, 1:80 and 1:160 represent *Erodium* dilutions with water. Water $2^{nd}$ EX (1:10) represents the second extraction cycle performed with the re-used *Erodium* mush. Levels not connected by same letter are significantly different. ACN-MET=Acetonitrile-Methanol (1:1). IL-8 reduction was calculated relatively to that obtained with cells stimulated only by TNF-α treatment.

Figure 8A:
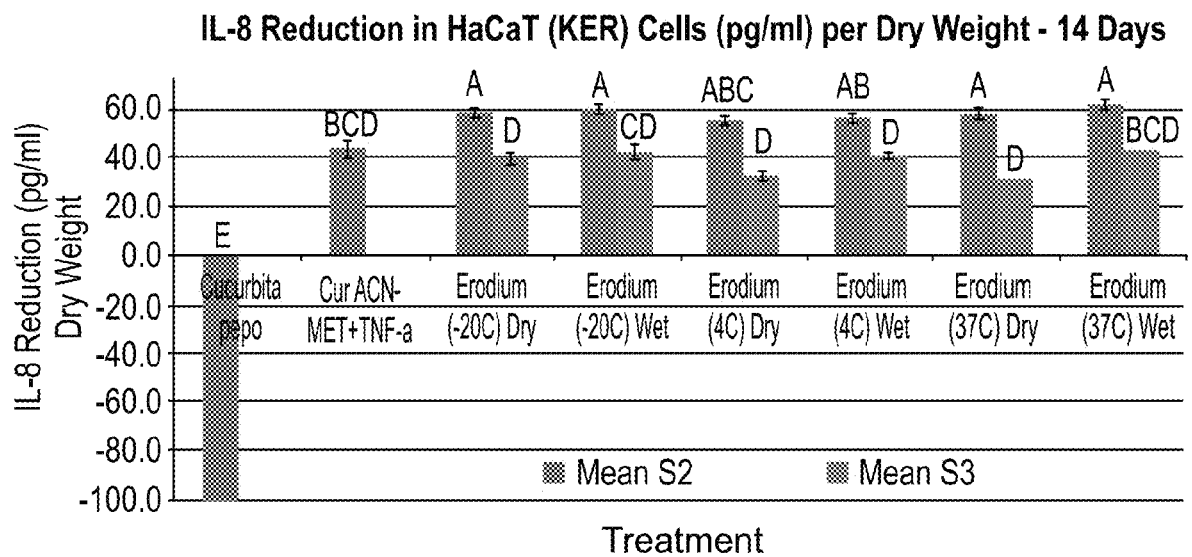
Figure 8B:
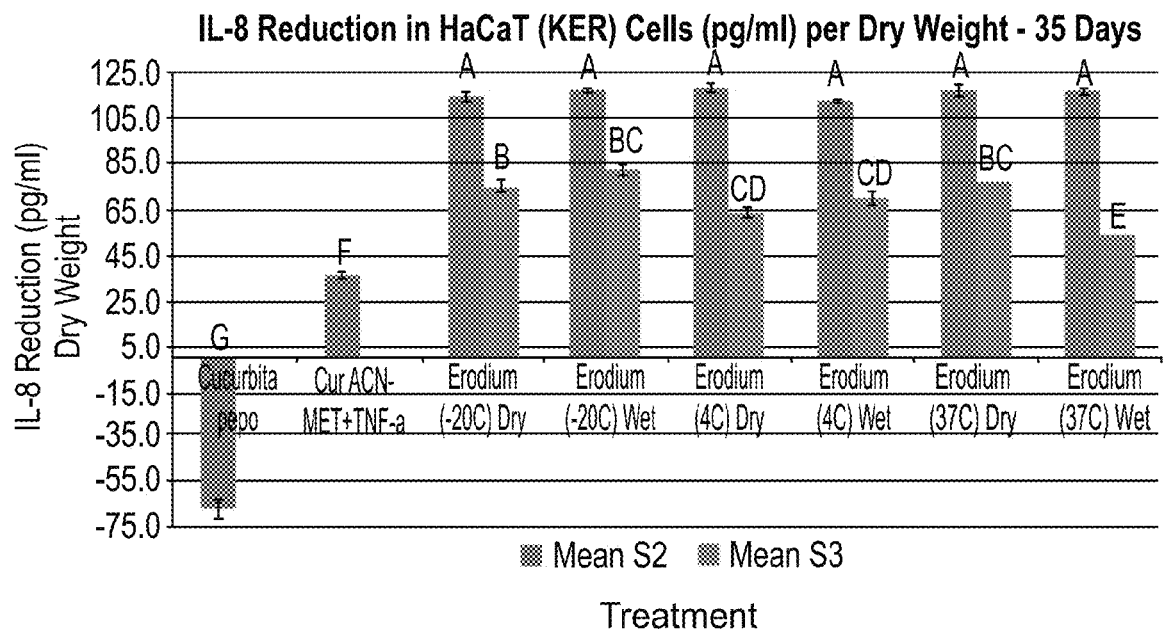

FIGS. 8A-B are graphs illustrating the anti-inflammatory activity and stability in *Erodium* water extracts prepared from S2 and S3 tubers. IL-8 ELISA assay was performed on HaCaT (KER) skin cells. Following extraction, samples were stored either dry or wet (re-suspended in water after sublimation) at (−20° C.), 4° C. and 37° C. for a period for either 2 or 5 weeks. (A) Activity and stability after 14 days. (B) Activity and stability after 35 days. Levels not connected by same letter are significantly different. ACN-MET=Acetonitrile-Methanol (1:1).

FIG. 9 is a graph illustrating the presence of anti-inflammatory activity in both peel and flesh of *Erodium* tubers. Activity was evaluated by IL-8 ELISA assay performed on HaCaT (KER) skin cells. Levels not connected by same letter are significantly different. ACN-MET=Acetonitrile-Methanol (1:1).

Figure 10A:
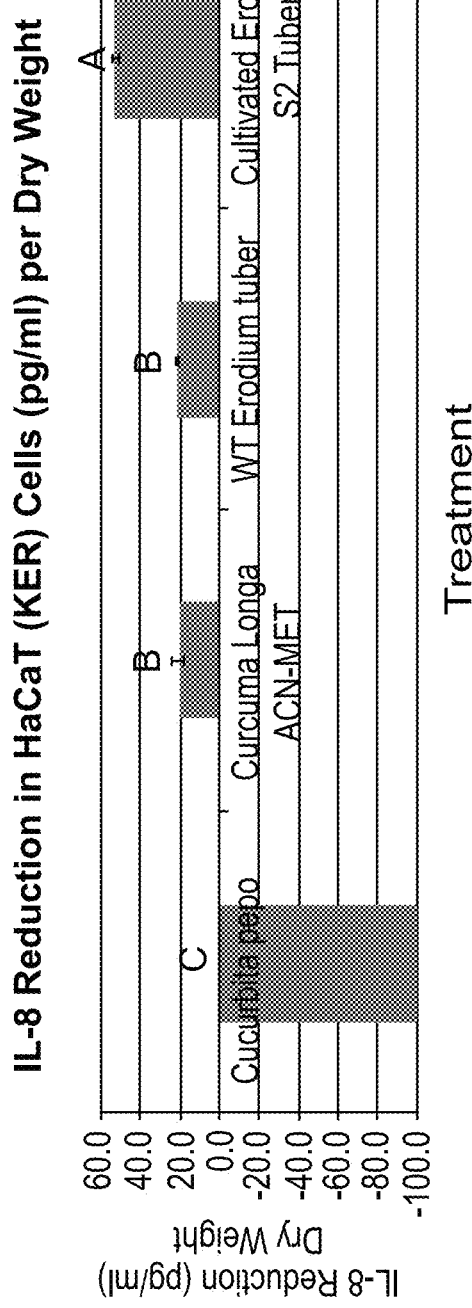
Figure 10B:
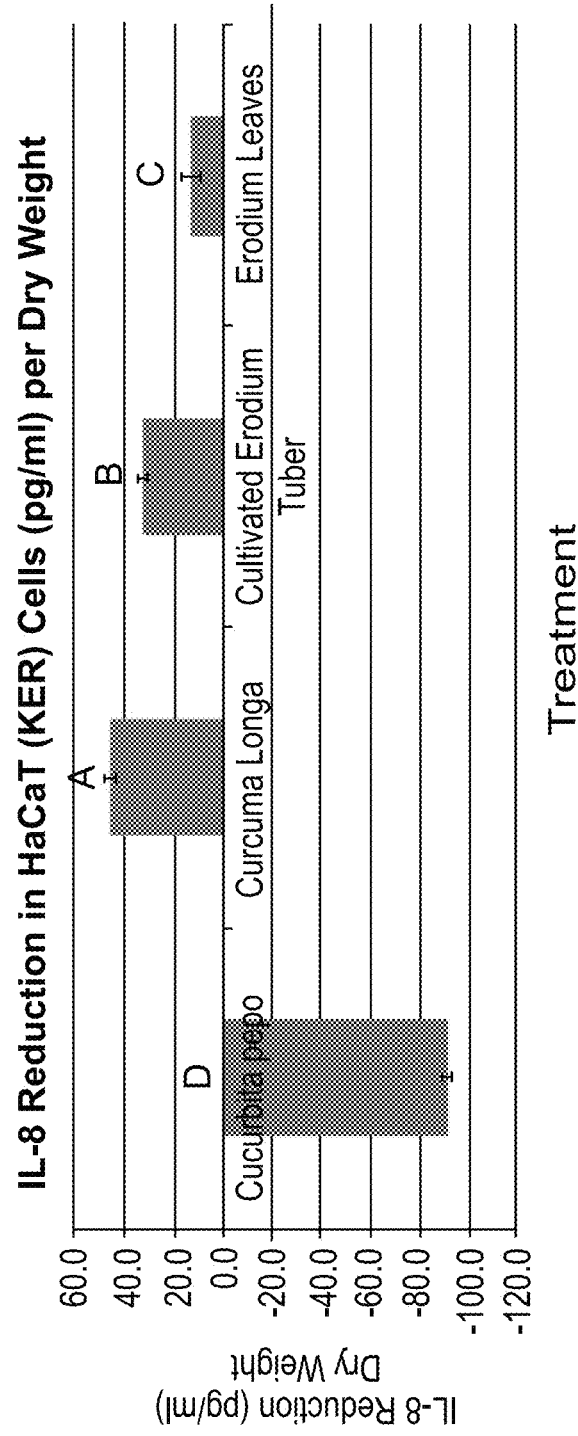

FIGS. 10A-B are graphs illustrating the anti-inflammatory activity comprised in wild type (WT) tubers and leaves of *Erodium* plants. Activity was evaluated by IL-8 ELISA assay performed on HaCaT (KER) skin cells. (A) Comparison of anti-inflammatory activity in WT tubers vs. cultivated tubers. (B) Comparison of anti-inflammatory activity in tubers vs. leaves of cultivated plants. Levels not connected by same letter are significantly different. ACN-MET=Acetonitrile-Methanol (1:1).

Figure 11A:
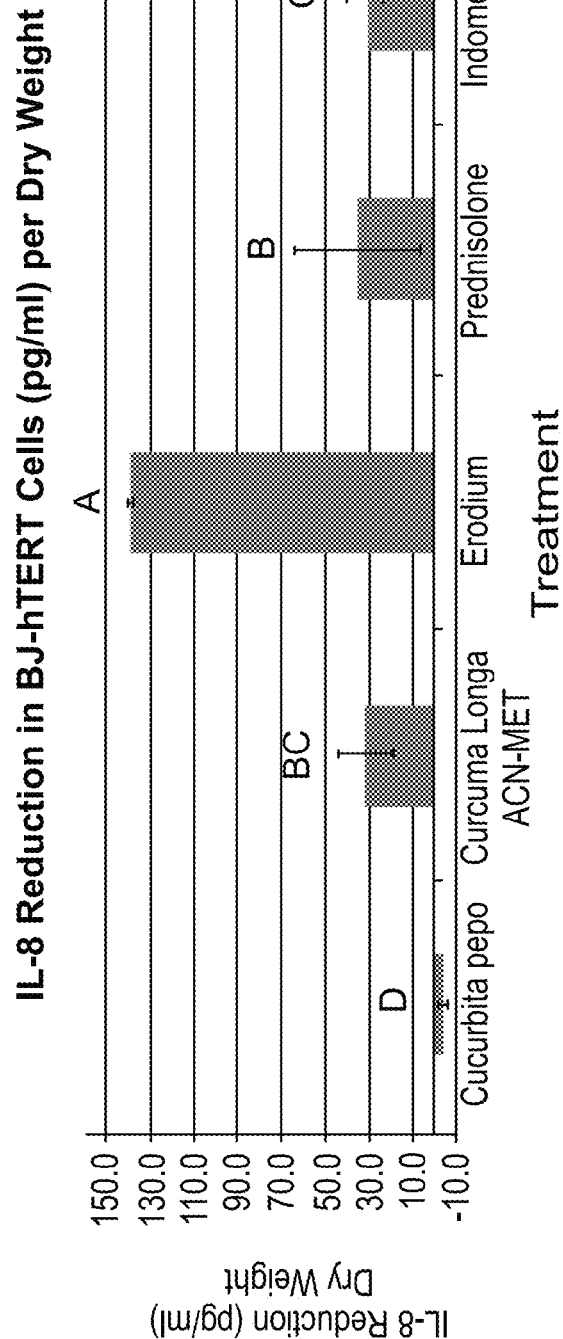
Figure 11B:
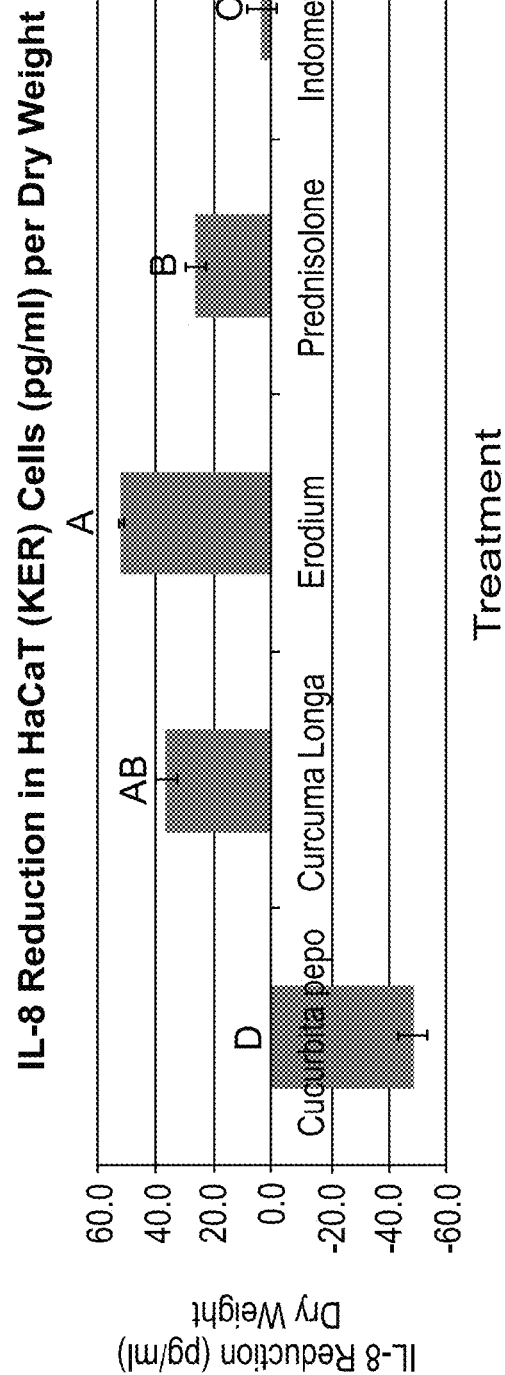
Figure 13A:
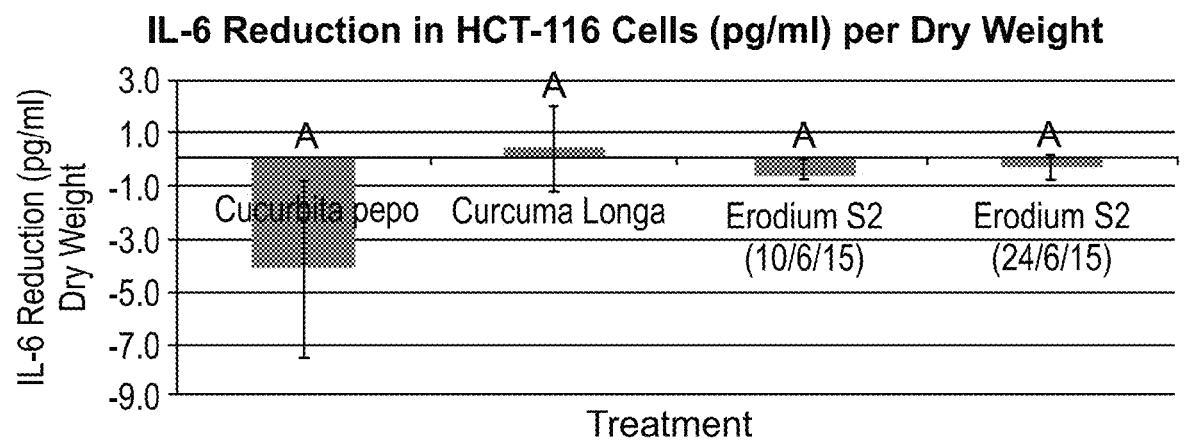
Figure 13B:
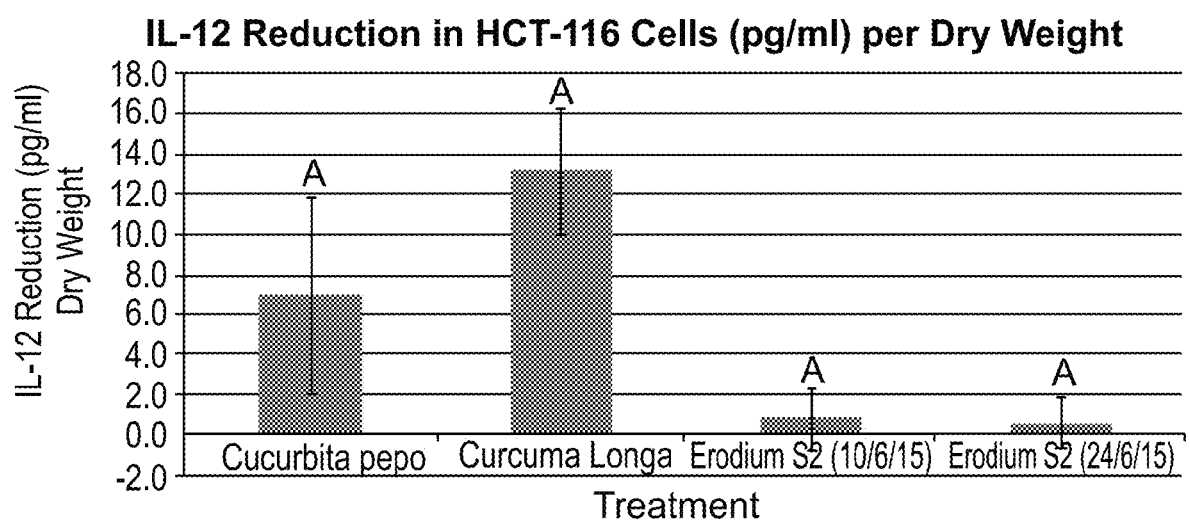
Figure 13C:
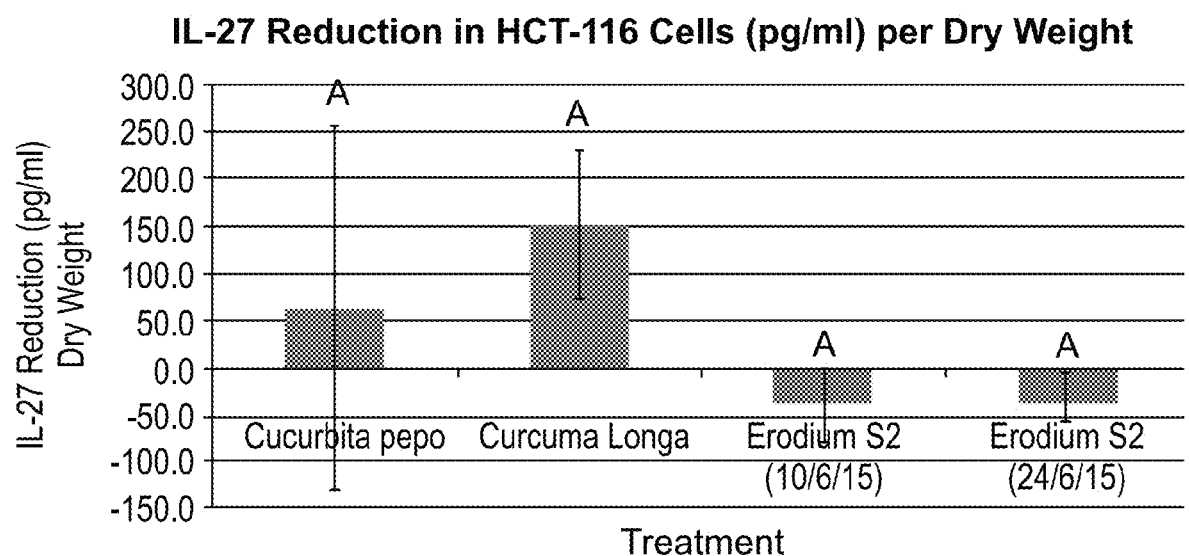
Figure 13D:
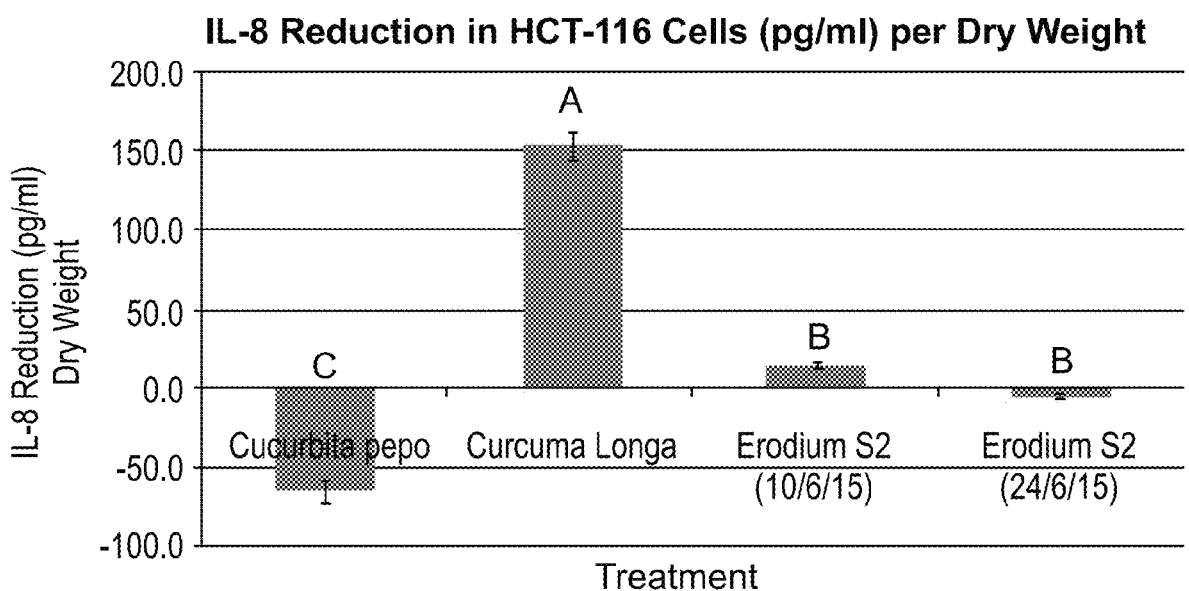
Figure 14C:
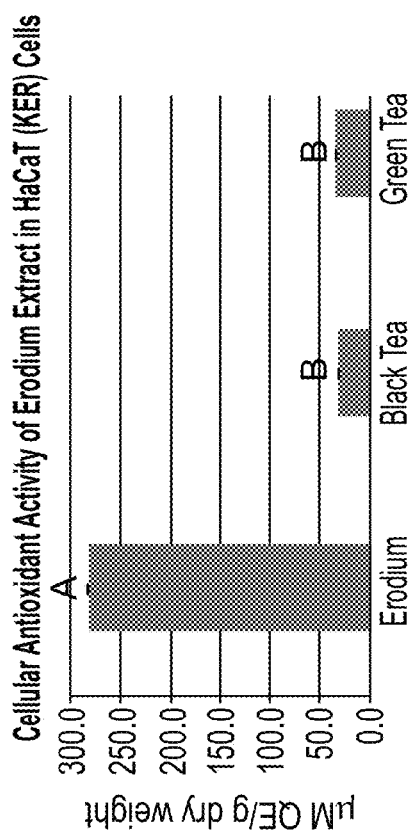
Figure 14D:
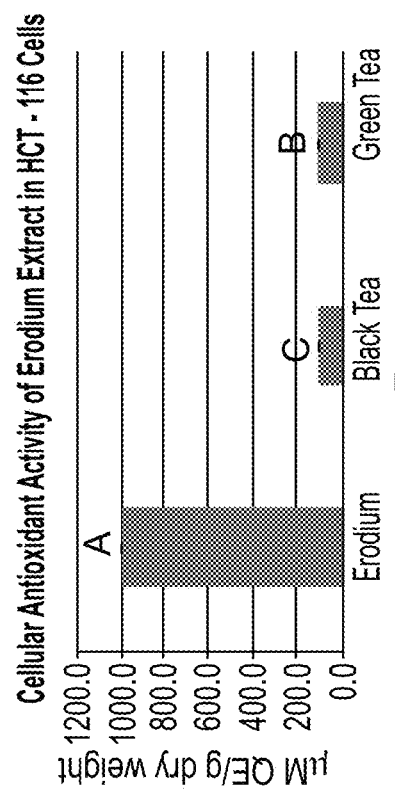
Figure 14A:
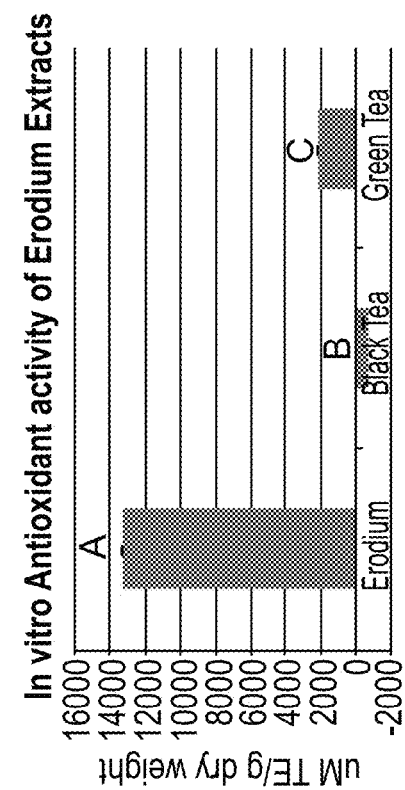
Figure 14B:
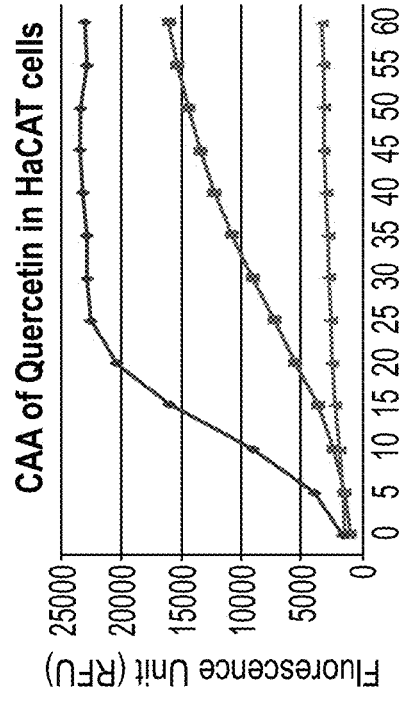

FIGS. 11A-B illustrate that *Erodium* water extracts can replace steroids and NSAIDs in inflammation treatment. Activity was evaluated by IL-8 ELISA assay performed in both BJ-hTERT (A) and HaCaT (KER) skin cells (B). Prednisolone and indomethacin working solutions were prepared as described in material and methods. Levels not connected by same letter are significantly different. ACN-MET=Acetonitrile-Methanol (1:1).

FIGS. 12A-B illustrate that *Erodium* water extracts alleviate inflammation caused by LPS on HCT-116 colon cells. (A) Expression of TNF-α and IL-8 during inflammation was evaluated at different time points (1, 4, 6 and 24 hr) after LPS treatment using the matching ELISA kit. (B) Cells were excited using 150 ng/ml LPS and treated with *Erodium* water extract. Levels not connected by same letter are significantly different.

FIGS. 13A-D illustrate the effect of *Erodium* water extracts on expression of IL-6, 11-12 and IL-27 in TNF-α stimulated HCT-116 cultured colon cells. Each cytokine was tested using the appropriate ELISA kit. Two different extractions Erodium extracts (Erodium S2 10/6/15 and Erodium S2 24/6/15) were tested. (A) Reduction of IL-6 levels. (B) Reduction of IL-12 levels. (C) Reduction of IL-27 levels. (D) Reduction of IL-8 levels. This assay (IL-8) served as a control for all other ELISA assays. Levels not connected by same letter are significantly different.

FIGS. 14A-D illustrate antioxidant activity found in Erodium water extracts. (A) antioxidant activity of Erodium water extracts in HaCaT (KER) skin cells. Bars represent the specific activity calculated as the area (manufacturer instructions) under the curve for each treatment relatively to the antioxidant activity of the standard Trolox™ divided by the dried weight of each extract. (B) Curves show the fluorescence unit obtained for non-treated (NT), Quercetin treated cells (blank) and cells treated with the Erodium extracts. (C) and (D) Assay in HaCaT (KER) skin cells (C) and HCT-116 colon cells (D). Bars represent specific activity calculated as the area (kit instructions) under the curve for each treatment relatively to the antioxidant activity of the standard Quercetin divided by the dried weight of each extract. Levels not connected by same letter are significantly different.

Figure 15A:
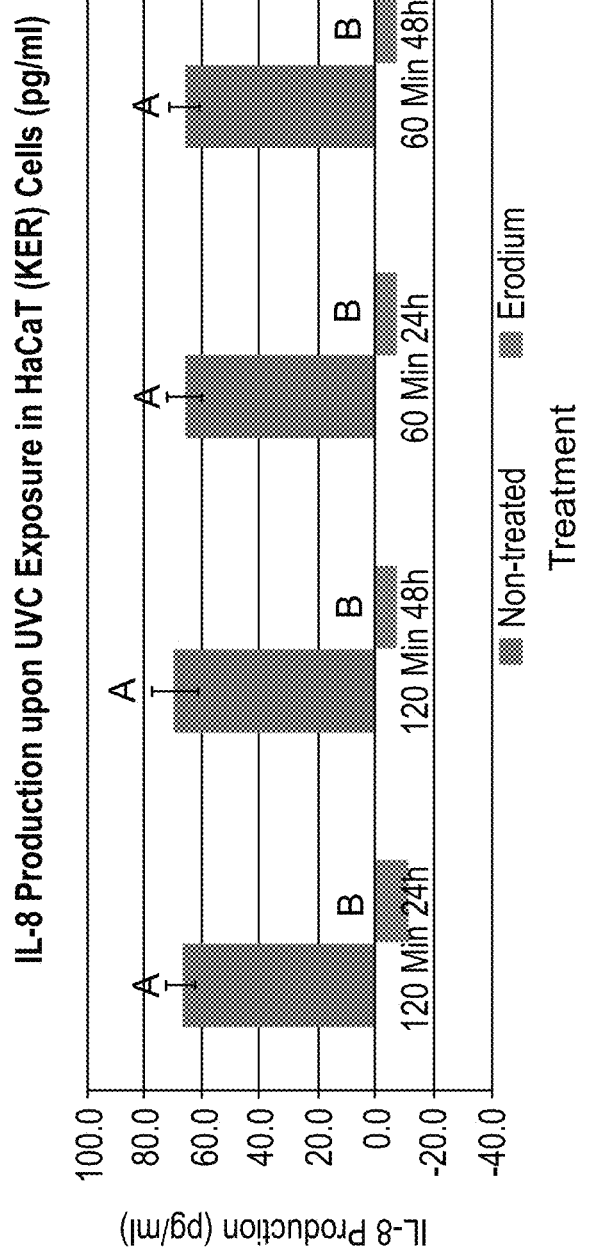
Figure 15B:
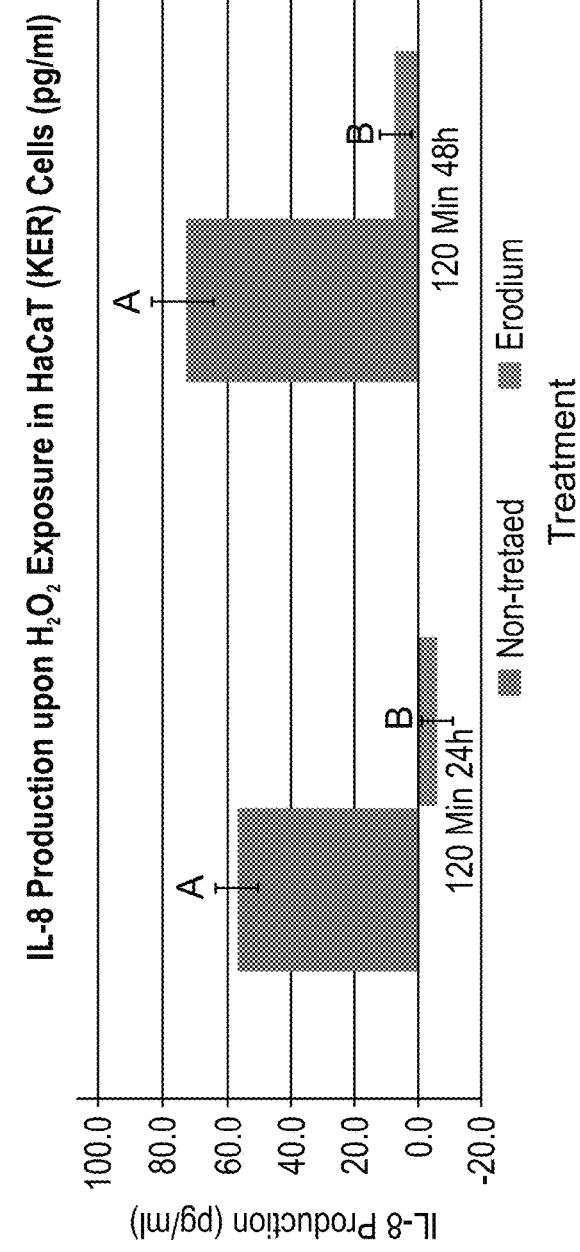

FIGS. 15A-B are graphs illustrating the anti-UV and hydrogen peroxide induced inflammatory activity of Erodium water extracts. HaCaT (KER) skin cells were exposed for 24 h or 48 h to either UVC or hydrogen peroxide ($H_2O_2$) in the presence or absence of Erodium water extract. Anti-pollutant activity was measured using the IL-8 ELISA assay. (A) Exposure to UVC. (B) Exposure to hydrogen peroxide ($H_2O_2$). Levels not connected by same letter are significantly different.

Figure 16:
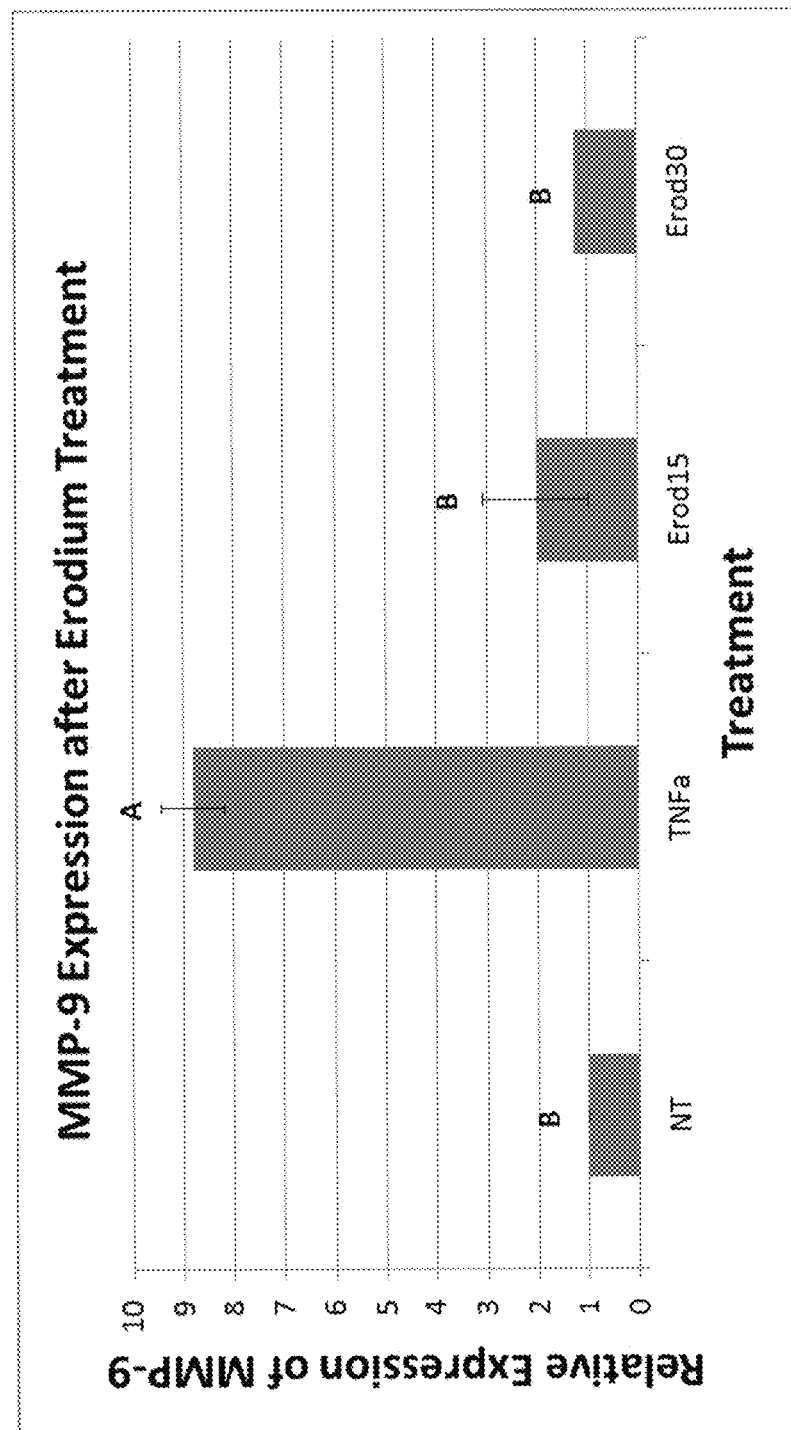

FIG. 16 is a graph illustrating the changes in MMP-9 expression upon treatment of HaCaT skin cells with Erodium water extract. Following TNF-α treatment, cells were treated with Erodium water extract. Erod5 and Erod10 are 5× and 10× dilutions respectively. Expression levels of MMP-9 were normalized to the expression of GAPDH mRNA and presented as the relative to GAPDH mRNA. Levels not connected by same letter are significantly different.

Figure 17:
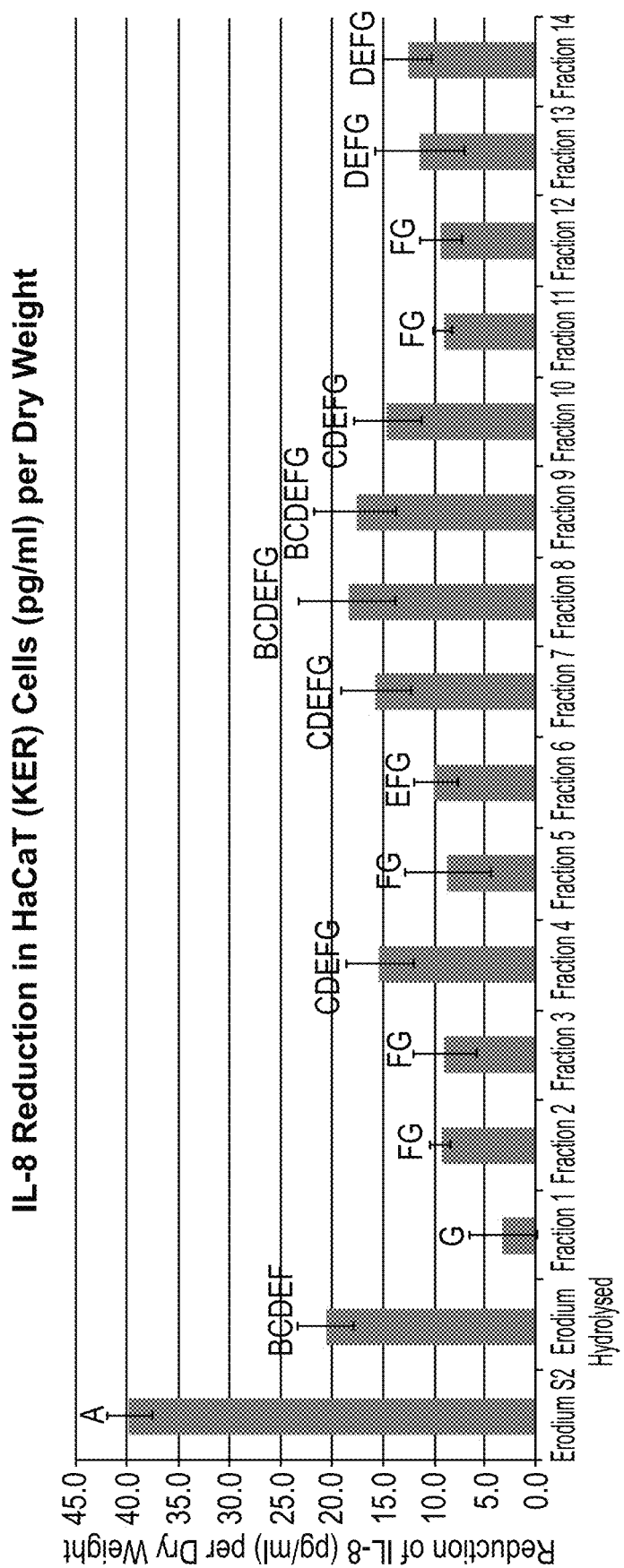

FIG. 17 is a graph illustrating the anti-inflammatory activity of peaks on HaCaT (KER) skin cells as detected by IL-8 ELISA assay. Levels not connected by same letter are significantly different.

DESCRIPTION OF SPECIFIC EMBODIMENTS OF THE INVENTION

The present invention, in some embodiments thereof, relates to extracts of Erodium plants and, more particularly, but not exclusively, to polar extracts of tubers of Erodium plants.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The Erodium Crassifolium plant has a Saharo-Arabian phytogeographic distribution. It is a perennial hemicryptophyte, the canopy of which is renewed from buds situated close to the soil surface. The storage organs are tubers, from one small (0.5 cm) spherical tuber in a young plant to between 3-6 larger elongated tubers (1-3 cm) that appear near the end of the roots.

Whilst investigating the medicinal properties of this plant, the present inventors noted that polar extracts of both the tubers and leaves comprised anti-inflammatory activity (FIGS. 2A-B, 3A-B, 9, 10A-B, 11A-B). The present inventors therefore propose that the extracts may be used in the treatment of inflammatory diseases.

The present inventors further found that the polar extracts showed antioxidant activity (FIGS. 14A-D) and anti-pollutant activity (FIGS. 15A-B), prompting their use for treating oxidative stress related disorders. Furthermore, the polar extracts may be used as cosmetics, especially in skin care related compositions.

Thus, according to a first aspect of the present invention, there is provided a method of generating a polar extract of an Erodium plant tissue comprising:

(a) contacting the Erodium plant tissue with a polar solvent under conditions to allow extraction of soluble agents from said Erodium plant tissue into said solvent to generate an extract; and (b) isolating the extract from said Erodium plant tissue, thereby generating the polar extract.

Erodium is a genus of flowering plants in the botanical family Geraniaceae. The genus includes about 60 species, native to North Africa, Indomalaya, The Middle East and Australia. They are perennials, annuals or subshrubs, with five-petalled flowers in shades of white, pink and purple, that strongly resemble the better-known Geranium (cranesbill). American species are known as filarees or heron's bill, whereas Eurasian ones are usually called storksbills in English.

Examples of Erodium species contemplated by the present inventors are set forth in Table 1, herein below.

TABLE 1

Erodium acaule (L.) Bech. & Thell.
Erodium aethiopicum (Lam.) Brumh. & Thell.
Erodium aureum
Erodium botrys (Cav.) Bertol.
Erodium brachycarpum (Godr.) Thell.
Erodium carolinianum
Erodium chium (L.) Willd.
Erodium chrysantum L'Hér. ex DC.
Erodium ciconium (L.) L'Hér.
Erodium cicutarium (L.) L'Hér.
Erodium corsicum Léman
Erodium crinitum
Erodium crispum Lapeyr.
Erodium crassifolium L'Her
Erodium cygnorum Nees
Erodium foetidum (L.) L'Hér.
Erodium glandulosum (Cav.) Willd.
Erodium gruinum (L.) L'Hér.
Erodium hoefftianum C. A. Meyer
Erodium laciniatum (Cav.) Willd.
Erodium lebelii Jord.
Erodium macrophyllum Hook. & Arn.
Erodium malacoides (L.) L'Hér.
Erodium manescavii Coss.
Erodium maritimum (L.) L'Hér.
Erodium moschatum (L.) L'Hér.
Erodium mouretii Pitard.
Erodium pelargoniflorum
Erodium reichardii
Erodium rodiei (Braun-Blanq.) Poirion
Erodium salzmannii Delile
Erodium texanum A. Gray
Erodium trifolium According to a particular embodiment, the Erodium plant is Erodium crassifolium L'Her.

The extract may be derived from a cultivated Erodium plant (i.e. not grown in their natural habitat) or may be derived from Erodium plants which grow in the wild. A method of growing *Erodium crassifolium* L'Her plants is described in the Examples section, herein below.

Thus, the present inventors contemplate planting seeds of *Erodium crassifolium* and harvesting the plant or the tubers prior to generation of the extract.

The tissue of the *Erodium* plant from which the extract is generated may be the leaves or the tubers. In particular, when the *Erodium* plant is *Erodium crassifolium* L'Her, the tissue may be leaves or tubers. When the *Erodium* plant is not *Erodium crassifolium* L'Her, the tissue is typically the tuber. Any size tuber is contemplated. In a particular embodiment, the tuber is between 0.5-4 cm in length, although more preferably between 1-3 cm in length and even more preferably between 2-3 cm in length.

Polar solvents suitable for use with the present invention include, but are not limited to, a $C_1$-$C_{10}$ compound having at least one heteroatom selected from: N, O, P, S, and combinations thereof. In some embodiments, the polar solvent includes at least one of: water, a $C_1$-$C_{10}$ alcohol, a $C_4$-$C_{10}$ ether, C $C_3$-$C_{10}$ aldehyde, a $C_3$-$C_{10}$ ketone, a $C_2$-$C_{10}$ carboxylic acid, a $C_2$-$C_{10}$ ester, a $C_3$-$C_{10}$ amine, a $C_1$-$C_5$ amide, and combinations thereof. In some embodiments, the polar solvent comprises a polar, protic solvent (e.g., methanol). In some embodiments, the polar solvent comprises a polar, aprotic solvent (e.g., acetone). Polar solvents suitable for use with the present invention include, but are not limited to, methanol, ethanol, n-propanol, iso-propanol, a butanol, a pentanol, acetone, methylethylketone, ethylacetate, acetonitrile, tetrahydrofuran, dimethylformamide, dimethylsulfoxide, water, and combinations thereof.

In particular embodiments, the extract is an aqueous extract.

In some embodiments, the polar solvent has a dielectric constant of about 5 or greater, about 10 or greater, about 15 or greater, about 20 or greater, about 25 or greater, about 30 or greater, or about 40 or greater.

In some embodiments, the polar solvent has a boiling point of about 200° C. or less, about 175° C. or less, about 150° C. or less, about 125° C. or less, or about 100° C. or less.

The concentration or amount of a polar solvent used to extract materials from the *Erodium* plant tissue can be varied. Generally, the ratio of a polar solvent to *Erodium* plant tissue (weight to weight) is the amount of a polar solvent sufficient to extract about 75% or more, about 85% or more, about 90% or more, about 95% or more, about 97% or more, or about 99% or more of a material having anti-inflammatory or anti-oxidative stress activity. For example, further processing of the *Erodium* plant tissue with an additional polar solvent after an initial extraction would provide about 25% or less, about 15% or less, about 10% or less, about 5% or less, about 3% or less, or about 1% or less of an *Erodium* plant tissue extract having anti-inflammatory/anti-oxidative stress activity in addition to that extracted by an initial extraction with a polar solvent. In some embodiments, the ratio of polar solvent to tuber is about 100:1 to about 1:100, or about 10:1 to about 1:10 by weight.

In some embodiments, the *Erodium* plant tissue is contacted with a polar solvent for about 15 minutes or more, about 30 minutes or more, about 1 hour or more, about 4 hours or more, about 8 hours or more, about 16 hours or more, about 24 hours or more, about 48 hours or more, or about 72 hours or more.

Temperature can also be controlled during the contacting. In some embodiments, the *Erodium* plant tissue is contacted with a polar solvent at a temperature of about −25° C. to about 200° C., about 0° C. to about 150° C., about 25° C. to about 100° C. or about 25° C. to about 35° C.

In some embodiments, the process of the present invention comprises isolating a liquid extract from the mixture comprising the liquid extract and solids. Suitable means for isolating the liquid extract include those known in the art of organic synthesis and include, but are not limited to, gravity filtration, suction and/or vacuum filtration, centrifuging, setting and decanting, and the like. In some embodiments, the isolating comprises filtering a liquid extract through a porous membrane, sponge, zeolite, paper, or the like having a pore size of about 100 μm or less, about 50 μm or less, about 20 μm or less, about 10 μm or less, about 5 μm or less, or about 1 μm or less.

The present inventors contemplate drying (i.e. removal of the polar solvent) and/or freezing the polar extract following generation.

The method for drying the extract (i.e. removing the polar solvent) is not particularly limited, and can include solvent evaporation at a reduced pressure (e.g., subatmospheric pressure) and/or an elevated temperature (e.g., above about 25° C.). The present invention also includes the removal of the polar solvent (and other process steps) being conducted under controlled temperature conditions such as, but not limited to, about 120° C. or less, about 100° C. or less, about 80° C. or less, about 60° C. or less, about 40° C. or less or about 30° C. or less. In some embodiments, it can be difficult to completely remove a polar solvent from a liquid extract by standard solvent removal procedures such as evaporation. In some embodiments, processes such as co-evaporation, lyophilization, and the like can be used to completely remove the polar solvent from a liquid fraction to form a dry powder, dry pellet, dry granulate, paste, and the like.

Following generation of the polar extract, the present inventors further contemplates additional purification steps so as to further purify active agents from the extract.

Thus, for example, the present inventors further propose fractionating the polar extract. Fractionating can be performed by processes such as, but not limited to: column chromatography, preparative high performance liquid chromatography ("HPLC"), reduced pressure distillation, and combinations thereof.

In some embodiments, the fractionating comprises applying the polar extract to an adsorbent and isolating an *Erodium* extract having anti-inflammatory activity or anti-oxidative stress activity by column chromatography. In some embodiments, the polar extract can be further purified using a chromatographic separation system comprising an adsorbent. In some embodiments, a chromatographic separation system further comprises a material in addition to an adsorbent, such as, but not limited to, a porous membrane, an ion exchange resin, a silica gel, a reverse phase silica gel, or any resin, polymer, colloid, and the like suitable for performing a separation based upon a molecular property such as, but not limited to, polarity, size, functional group, and combinations thereof.

In some embodiments, an adsorbent is porous. In some embodiments, a porous adsorbent has a pore size of about 20 nm or less, about 15 nm or less, about 10 nm or less, about 8 nm or less, about 6 nm or less, about 5 nm or less, about 4 nm or less, about 3 nm or less, about 2 nm or less, or about 1 nm or less. In some embodiments, a porous adsorbent has a pore size of about 0.6 nm to about 20 nm, about 0.8 nm to about 15 nm, about 1 nm to about 10 nm, about 1.5 nm to about 8 nm, about 2 nm, about 4 nm, about 6 nm, or about 8 nm.

Exemplary adsorbents suitable for use with the present invention include, but are not limited to, cross-linked styrene-divinylbenzene resins (e.g., DOWEX® OPTIPORE® Resins, The Dow Chemical Co., Midland, Mich. and AMBERLITE® XAD4, XAD16, XAD1180, and XAD1600, Rohm and Haas Co., Philadelphia, Pa.); highly cross-linked, aliphatic, or phenol-formaldehyde condensate polymers (e.g., AMBERLITE® XAD7IIP and XAD761, Rohm and Haas Co.); carbonaceous resins (e.g., AMBERSORB® 563 and 572, Rohm and Haas Co.); granular activated carbon (e.g., FILTRASORB® 300 and 400, Calgon Carbon Corp., Pittsburgh, Pa.); and combinations thereof.

An eluting solvent is applied to an adsorbent loaded with the aqueous extract to elute fractions from the adsorbent. In some embodiments, an eluting solvent is an aqueous eluent comprising water. In some embodiments, an eluting solvent is deionized (e.g., deionized water). Alternatively, the tonicity of an eluting solvent can be increased by including one or more ions, salts, and the like to an eluting solvent.

In some embodiments, an eluting solvent comprises an "organic," which as used herein refers to a liquid, solid, or gas that includes at least one carbon atom in its molecular structure. Organics suitable for use as eluting solvents include, but are not limited to, methanol, ethanol, propanol, acetone, carbon dioxide, methylethyl ketone, acetonitrile, butyronitrile, carbon dioxide, ethyl acetate, tetrahydrofuran, di-iso-propylether, ammonia, triethylamine, N,N-dimethylformamide, N,N-dimethylacetamide, and the like, and combinations thereof. In some embodiments, an eluting solvent comprises an organic and water, e.g., about 95% ethanol and about 5% water.

The polar extracts and/or agents purified therefrom may be tested for anti-inflammatory activity and/or anti oxidative stress activity and/or anti-aging activity.

Exemplary methods for testing the above mentioned activities are described in the Examples section herein below.

Other methods for testing the activity of the extract (or agents isolated therefrom) for anti-oxidant activity are detailed in the article Am J Clin Nutr January 2005 vol. 81 no. 1 261S-267S by Andrew Collins.

For testing the effect of the extract (or agents isolated therefrom) on inflammation, in vitro assays may be used to which analyze the effect on cell derived factors such as IFN-gamma, IL-8, leukotriene B4, nitric oxide, prostaglandins, TNF-alpha and IL-1. Many in vivo assays are known in the art for testing anti-inflammatory activity and are contemplated by the present invention.

The extract of the present invention can also be characterized by analytical methods such as, but not limited to, spectroscopic methods such as, but not limited to, ultraviolet-visible spectroscopy ("UV-Vis"), infrared spectroscopy ("IR"), and the like; mass-spectrometry ("MS") methods such as, but not limited to, time-of-flight MS; quadrupole MS; electrospray MS, Fourier-transform MS, Matrix-Assisted Laser Desorption/Ionization ("MALDI"), and the like; chromatographic methods such as, but not limited to, gas-chromatography ("GC"), liquid chromatograph ("LC"), high-performance liquid chromatography ("HPLC"), and the like; and combinations thereof (e.g., GC/MS, LC/MS, HPLC/UV-Vis, and the like), and other analytical methods known to persons of ordinary skill in the art.

The present invention is also directed to a product prepared by the process of the present invention. In some embodiments, the *Erodium* extract of the present invention is a polar extract (e.g. aqueous extract) and is substantially free of cytotoxic compounds. In some embodiments, the *Erodium* extract of the present invention substantially lacks cytotoxic activity. As used herein, "substantially lacks cytotoxic activity" refers to extracts that are not appreciably cytotoxic under in vitro or in vivo testing and/or administering conditions. In some embodiments, "substantially lacks cytotoxic activity" refers to extracts lacking cytotoxic activity as described in S. B. Ullman et al., Exp. Med. Sur. 3:11 (1945) and S. B. Ullman et al, Exp. Med. Sur. /0:287 (1952), both of which are incorporated herein by reference in their entirety.

In one embodiment, the polar extracts derived from *Erodium* plants (e.g. from the tubers and/or leaves), do not comprise plant tissue or other water insoluble components.

In other embodiments, the polar extracts derived from *Erodium* plants (e.g. from the tubers and/or leaves), have not been boiled for more than 20 minutes, more preferably no more than 10 minutes and even more preferably have not been boiled for more than 1 minute.

In still other embodiments, the extract does not comprise material from more than five plants of different species, more than four plants of different species, more than three plants of different species, or even more than two plants of different species.

Since the extracts of the present invention or active agents derived therefrom have anti-inflammatory activity and/or antioxidant activity, they may be used for treating diseases or disorders related thereto.

Thus, according to another aspect of the present invention there is provided a method of treating an inflammatory disease or a disease related to oxidative stress in a subject in need thereof comprising administering to the subject a therapeutically effective amount of a polar extract of tubers of an *Erodium* plant, thereby treating the disease.

As used herein the phrase "oxidative stress" refers to an undesirable imbalance where oxidants outnumber antioxidants. This situation can arise if the rate of ROS production overwhelms existing antioxidant defenses. In such circumstances, a series of cellular responses can occur that can lead to an even greater increase in ROS production. Excessive ROS production and its otherwise ineffective regulation can be detrimental to cells and tissues, inducing cellular damage that ultimately can lead to cell death (apoptosis). Oxidative stress-associated damage also can cause undesirable changes to the structural and functional integrities of cells that can lead to the propagation of cells instead of apoptosis. Additionally, oxidatively-damaged cellular macromolecules can trigger immune responses that can lead to disease. See generally, D. G. Lindsay et al. (2002) Mol. Aspects of Med. 23:1-38, incorporated herein by reference.

It will be appreciated that oxidative stress may be responsible for initiating or otherwise causing disease. Alternatively, or additionally, the progression of the disease can be affected by any resultant oxidative stress.

Hence the phrase "oxidative stress related disease" as used herein, refers to a disease or medical condition (including syndromes) wherein the onset or progression thereof is promoted by oxidative stress. Since oxidative stress is believed to be responsible for the pathogenesis of many neurological, heart, malignant and age-associated diseases, the present invention contemplates all such diseases including for example, atherosclerosis, autoimmune diseases, cancer, cardiovascular disease, cataract, dementia, diabetes and diabetic vasculopathy, and neurodegenerative diseases.

Exemplary neurodegenerative diseases include, but are not limited to Parkinson's disease, Multiple Sclerosis, ALS, multi-system atrophy, Alzheimer's disease, stroke, progressive supranuclear palsy, fronto-temporal dementia with parkinsonism linked to chromosome 17 and Pick's disease.

Inflammatory Diseases—include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2): 140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lymphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to a particular embodiment, the extracts of the present invention are not used to treat epilepsy.

The extract may be administered to the subject per se or may be provided as part of a pharmaceutical composition.

The purpose of a pharmaceutical composition is to facilitate administration of an active ingredient (herein the *Erodium* extract) to an organism (e.g., a human being). Pharmaceutical compositions may be manufactured by processes well known in the art, e.g., by means of conventional mixing, dissolving, granulating, dragee-making, levigating, emulsifying, encapsulating, entrapping or lyophilizing processes.

Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include without limitation, calcium carbonate, calcium phosphate, various sugars and types of starch, cellulose derivatives, gelatin, vegetable oils, polyethylene glycols, sodium stearate, glycerol monostearate, talc, sodium chloride, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Further techniques for formulation and administration of active ingredients may be found in "Remington's Pharmaceutical Sciences," Mack Publishing Co., Easton, Pa., latest edition, which is incorporated herein by reference as if fully set forth herein.

The pharmaceutical compositions herein described may also comprise suitable solid or gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions for use in accordance with the present invention thus may be formulated in conventional manner using one or more pharmaceutically acceptable carriers comprising excipients and auxiliaries, which facilitate processing of the active ingredients into preparations which, can be used pharmaceutically. Proper formulation is dependent upon the route of administration chosen.

Formulations for oral delivery can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should be suitable for the mode of administration.

For oral administration, the active ingredients can be formulated readily by combining the active ingredients with pharmaceutically acceptable carriers well known in the art. Such carriers enable the active ingredients of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For transdermal administration, the composition can be formulated in a form of a gel, a cream, an ointment, a paste, a lotion, a milk, a suspension, an aerosol, a spray, a foam, a serum, a swab, a pledget, a pad or a patch. Formulations for transdermal delivery can typically include carriers such as water, liquid alcohols, liquid glycols, liquid polyalkylene glycols, liquid esters, liquid amides, liquid protein hydrolysates, liquid alkylated protein hydrolysates, liquid lanolin, lanolin derivatives, glycerin, mineral oil, silicone, petroleum jelly, lanolin, fatty acids, vegetable oils, parabens, waxes, and like materials commonly employed in topical compositions. Various additives, known to those skilled in the art, may be included in the transdermal formulations of the invention. For example, solvents may be used to solubilize certain active ingredients substances. Other optional additives include skin permeation enhancers, opacifiers, antioxidants, gelling agents, thickening agents, stabilizers, and the like.

For buccal administration, the compositions may take the form of tablets or lozenges formulated in conventional manner.

For injection, the active ingredients of the pharmaceutical composition may be formulated in aqueous solutions, preferably in physiologically compatible buffers such as Hank's solution, Ringer's solution, or physiological salt buffer.

For administration by inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient and a suitable powder base such as lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The composition can be formulated as rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Examples of suitable coating materials include, but are not limited to, cellulose polymers such as cellulose acetate phthalate, hydroxypropyl cellulose, hydroxypropyl methylcelhilose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers", are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as *acacia*, tragacanth, sodium alginate, cellulose, including hydroxypropyhnethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-β-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The compounds may be complexed with other agents as part of their being pharmaceutically formulated. The pharmaceutical compositions may take the form of, for example, tablets or capsules prepared by conventional means with pharmaceutically acceptable excipients such as binding agents (e.g., *acacia*, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, *acacia*, sucrose, microcrystalline cellulose, kaolin, mannitol, dicalcium phosphate, calcium carbonate, sodium chloride, or alginic acid); lubricants (e.g., magnesium stearates, stearic acid, silicone fluid, talc, waxes, oils, and colloidal silica); and disintegrators (e.g., micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the compounds and their physiologically acceptable solvates may be formulated for administration.

Liquid formulations for oral administration prepared in water or other aqueous vehicles may contain various suspending agents such as methylcellulose, alginates, tragacanth, pectin, kelgin, carrageenan, *acacia*, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human.

The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1).

Dosage amount and interval may be adjusted individually so that sufficient amount of the active agents present in the extract reach the appropriate cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

The *Erodium* extract of the present invention can be administered to a subject (e.g., a human or animal) in need thereof in a variety of other forms including a nutraceutical composition or a cosmetic composition.

As used herein, a "nutraceutical composition" refers to any substance that may be considered a food or part of a food and provides medical or health benefits, including the prevention and treatment of disease. In some embodiments, a nutraceutical composition is intended to supplement the diet and contains at least one or more of the following ingredients: a vitamin; a mineral; an herb; a botanical; a fruit; a vegetable; an amino acid; or a concentrate, metabolite, constituent, or extract of any of the previously mentioned ingredients; and combinations thereof.

In some embodiments, a nutraceutical composition of the present invention can be administered as a "dietary supplement," as defined by the U.S. Food and Drug Administration, which is a product taken by mouth that contains a "dietary ingredient" such as, but not limited to, a vitamin, a mineral, an herb or other botanical, an amino acid, and substances such as an enzyme, an organ tissue, a glandular, a metabolite, or an extract or concentrate thereof.

Non-limiting forms of nutraceutical compositions of the present invention include: a tablet, a capsule, a softgel, a gelcap, a liquid, a powder, a solution, a tincture, a suspension, a syrup, or other forms known to persons of skill in the art. A nutraceutical composition can also be in the form of a food, such as, but not limited to, a food bar, a beverage, a food gel, a food additive/supplement, a powder, a syrup, and combinations thereof.

In one embodiment, the nutraceutical composition is not formulated in a honey.

Since the extracts of the present invention comprise anti-oxidant activity and anti-inflammatory activity as well as protecting against UV radiation, the present inventors contemplate that another use thereof is in cosmetic compositions for treating the skin. Thus, the agents of the present invention may be formulated for cosmetics.

Suitable cosmetic formulations contemplated by the present invention include, but are not limited to a cream, a face mask, a scrub, a soap, a wash or a gel.

Thus, according to another aspect of the present invention there is provided a cosmetic care method comprising applying to at least one body zone (e.g. face) in need thereof of an efficient amount of a composition comprising an *Erodium* extract as defined herein. According to a particular embodiment, the method is for moisturizing the skin, and/or for protecting it against any type of stress, and/or alternatively for producing an antiaging effect.

Such compositions typically comprise dermatologically acceptable carriers suitable for external topical application.

The cosmetic composition according to the present invention may further comprise at least one pharmaceutical adjuvant known to the person skilled in the art, selected from thickeners, preservatives, fragrances, colorants, chemical or mineral filters, moisturizing agents, thermal spring water, etc.

The composition may comprise at least one agent selected from a sebum-regulating agent, an antibacterial agent, an antifungal agent, a keratolytic agent, a keratoregulating agent, an astringent, an anti-inflammatory/anti-irritant, an antioxidant/free-radical scavenger, a cicatrizing agent, an anti-aging agent and/or a moisturizing agent.

The term "sebum-regulating agent" refers, for example, to 5-α-reductase inhibitors, notably the active agent 5-α-Avocuta® sold by Laboratoires Expanscience. Zinc and gluconate salts thereof, salicylate and pyroglutamic acid, also have sebum-suppressing activity. Mention may also be made of spironolactone, an anti-androgen and aldosterone antagonist, which significantly reduces the sebum secretion rate after 12 weeks of application. Other extracted molecules, for example from seeds of the pumpkin *Cucurbita pepo*, and squash seed oil, as well as palm cabbage, limit sebum production by inhibiting 5-α-reductase transcription and activity. Other sebum-regulating agents of lipid origin that act on sebum quality, such as linoleic acid, are of interest.

The terms "anti-bacterial agent" and "antifungal agent" refer to molecules that limit the growth of or destroy pathogenic microorganisms such as certain bacteria like *P. acnes* or certain fungi (*Malassezia furfur*). The most traditional are preservatives generally used in cosmetics or nutraceuticals, molecules with anti-bacterial activity (pseudo-preservatives) such as caprylic derivatives (caprylolyl glycine, glyceryl caprylate, etc.), such as hexanediol and sodium levulinate, zinc and copper derivatives (gluconate and PCA), phytosphingosine and derivatives thereof, benzoyl peroxide, piroctone olamine, zinc pyrithione, selenium sulfide, econazole, ketoconazole, or local antibiotics such as erythromycin and clindamycin, etc.

The terms "keratoregulating agent" and "keratolytic agent" refer to an agent that regulates or helps the elimination of dead cells of the stratum corneum of the epidermis. The most commonly used keratoregulating/keratolytic agents include: alpha-hydroxy acids (AHAs) of fruits (citric acid, glycolic acid, malic acid, lactic acid, etc.), AHA esters, combinations of AHAs with other molecules such as the combination of malic acid and almond proteins (Keratolite®), the combination of glycolic acid or lactic acid with arginine or the combination of hydroxy acid with lipid molecules such as LHA® (lipo-hydroxy acid), amphoteric hydroxy acid complexes (AHCare), willow bark (*Salix alba* bark extract), azelaic acid and salts and esters thereof, salicylic acid and derivatives thereof such as capryloyl salicylic acid or in combination with other molecules such as the combination of salicylic acid and polysaccharide (beta-hydroxy acid, or BHA), tazarotene, adapalene, as well as molecules of the retinoid family such as tretinoin, retinaldehyde, isotretinoin and retinol.

The term "astringent" refers to an agent that helps constrict pores, the most commonly used being polyphenols, zinc derivatives and witch hazel.

Exemplary anti-inflammatory/anti-irritant agents that may be included in the cosmetic compositions include glycyrrhetinic acid (licorice derivative) and salts and esters thereof, alpha-bisabolol, *Ginkgo biloba*, Calendula, lipoic acid, beta-carotene, vitamin B3 (niacinamide, nicotinamide), vitamin E, vitamin C, vitamin B12, flavonoids (green tea, quercetin, etc.), lycopene or lutein, avocado sugars, avocado oleodistillate, arabinogalactan, lupin peptides, lupin total extract, *quinoa* peptide extract, Cyloceramide'® (oxazoline derivative), anti-glycation agents such as carnosine, N-acetyl-cysteine, isoflavones such as, for example, genistein/genistin, daidzein/daidzin, spring water or thermal spring water (eau d'Avene, eau de la Roche Posay, eau de Saint Gervais, eau d'Uriage, eau de Gamarde), goji extracts (*Lycium barbarum*), plant amino acid peptides or complexes, topical dapsone, or anti-inflammatory drugs.

Exemplary antioxidants/free-radical scavengers that may be used in combination are advantageously selected from the group comprised of thiols and phenols, licorice derivatives such as glycyrrhetinic acid and salts and esters thereof, alpha-bisabolol, *Ginkgo biloba* extract, Calendula extract, Cyloceramide® (oxazoline derivative), avocado peptides, trace elements such as copper, zinc and selenium, lipoic acid, vitamin B12, vitamin B3 (niacinamide, nicotinamide), vitamin C, vitamin E, coenzyme Q10, hill, glutathione, butylated hydroxytoluene (BHT), butylated hydroxyanisole (BHA), lycopene or lutein, beta-carotene, the family of polyphenols such as tannins, phenolic acids, anthocyanins, flavonoids such as, for example, extracts of green tea, of red berries, of cocoa, of grapes, of *Passiflora incarnata* or of Citrus, or isoflavones such as, for example, genistein/genistin and daidzein/daidzin. The group of antioxidants further includes anti-glycation agents such as carnosine or certain peptides, N-acetyl-cysteine, as well as antioxidant or free-radical scavenging enzymes such as superoxide dismutase (SOD), catalase, glutathione peroxidase, thioredoxin reductase and agonists thereof.

The agents that cicatrize/repair the barrier function which may be used in combination are advantageously vitamin A, panthenol (vitamin B5), Avocadofurane®, avocado sugars, lupeol, maca peptide extract, *quinoa* peptide extract, arabinogalactan, zinc oxide, magnesium, silicon, madecassic or asiatic acid, dextran sulfate, coenzyme Q10, glucosamine and derivatives thereof, chondroitin sulfate and on the whole glycosaminoglycans (GAGs), dextran sulfate, ceramides, cholesterol, squalane, phospholipids, fermented or unfermented soya peptides, plant peptides, marine, plant or biotechnological polysaccharides such as algae extracts or fern extracts, trace elements, extracts of tannin-rich plants such as tannins derived from gallic acid called gallic or hydrolysable tannins, initially found in oak gall, and catechin tannins resulting from the polymerization of flavan units whose model is provided by the *catechu (Acacia catechu)*. The trace elements that may be used are advantageously selected from the group comprised of copper, magnesium, manganese, chromium, selenium, silicon, zinc and mixtures thereof.

The anti-aging agents that can act in combination to treat acne in mature subjects are antioxidants and in particular vitamin C, vitamin A, retinol, retinal, hyaluronic acid of any molecular weight, Avocadofurane® lupin peptides and maca peptide extract.

The most commonly used moisturizers/emollients are glycerin or derivatives thereof, urea, pyrrolidone carboxylic acid and derivatives thereof, hyaluronic acid of any molecular weight, glycosaminoglycans and any other polysaccharides of marine, plant or biotechnological origin such as, for example, xanthan gum, Fucogel®, certain fatty acids such as lauric acid, myristic acid, monounsaturated and polyunsaturated omega-3, -6, -7 and -9 fatty acids (linoleic acid, palmitoleic acid, etc.), sunflower oleodistillate, avocado peptides and cupuacu butter.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Examples

Reference is now made to the following examples, which together with the above descriptions illustrate some embodiments of the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074;

4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Growth Protocol of *Erodium crassifolium* Plants

Seeding was done in 1.5 meter planting beds (from center to center) in two strips 40 cm away from each other and irrigated with a drip irrigation system in which droppers were places every 20 cm. Total number of plants in one meter—10. Seeding was carried out in December.

Fertilization with a 6:6:6 fertilizer containing 3% microelements and 50-60 ppm concentration of nitrogen (about 750 ml per cubic meter) started immediately after germination. Irrigation regime was 2 cubic meters per hectare per day once every two days. After beginning of flowering, fertilization with a 4:2:6 fertilizer was performed with a dose of 100 ppm nitrogen, i.e. two liters per cubic meter. Water quantities rise to 3 cubic meters per day in March, and up to five cubic meters per day in April.

Harvesting of tubers begins in late April early May and ends in mid-May. Harvesting is done by manual excavation and removal of tubers. A seed collection step (April) to be used for next season (December) is performed prior to tuber harvesting. Total growing protocol takes approximately 5 months.

*Erodium crassifolium* and *Cucurbita pepo* Extracts

Ethyl Acetate Extraction:
Bulbs collected from Ramat Negev and stored in dark room, at room temperature after collection in the field, were frozen at −80° C. Twenty five grams of frozen bulbs were blended in a blender at top speed for 1 min in acetone (1:5 w/v), extracted in ethyl acetate and washed with potassium phosphate buffer (0.2 M, pH 8.3). Extracts were dried over anhydrous $Na_2SO_4$ and concentrated in vacuo and stored at −20° C. for further analysis.

Extraction in Solvents with Different Polarity Traits:
Four different solvents with different polarity traits were used for extractions: $H_2O$—the most hydrophilic solvent, 70% ETOH or Acetonitrile:Methanol (1:1) for medium polar solvents and Hexane:Ethyl:Acetate (1:1) for hydrophobic solvents. *Erodium crassifolium* bulbs were crushed using a mortar and pestle. For extractions using water, two grams of the crushed material were transferred to a 15 ml falcon tube and 4 ml of water were added. For the other solvents, two grams of the crushed material were transferred to 50 ml falcon tubes and 20 ml of the corresponding solvent were added. All tubes were incubated overnight at 28° C. with shaking at 180 rpm. Tubes for water extraction were stored at 4° C. prior to drying. The dried material was stored for further analysis. Tubes containing the other solvents were centrifuged for 5 minutes at 2500 rpm. Equal volumes of the supernatant was transferred to two 15 ml falcon tubes that were then dried and concentrated in vacuo overnight and stored at −20° C. for further analysis.

For extracts which were prepared with either 70% ETOH, Acetonitrile:Methanol (1:1) or Hexane:Ethyl:Acetate (1:1), the dried material was dissolved in 100 µl of the solvent used for extraction followed by addition of 900 µl of culture media (McCoy's 5a Medium Modified or DMEM). The obtained solution was then spun for 1 min at 14,000 rpm followed by filtration through a 0.45 µm. For water extracts, 1 ml double distilled water was added to the dried extracts which were then filtered using a 0.45 µm filter. *Curcubita pepo* extractions in water were carried out similarly. Unless stated differently, cells were treated with a 1:10 dilution of plant extracts.

Determination of Dry Weight:
1 gr of crushed material was wrapped in aluminum foil and the total weight was recorded. After overnight incubation at 60° C., the material was reweighed.

Preparation of *Curcuma longa* Solutions:
A 400 mg commercial pill of *curcuma longa* extract was dissolved in 1 ml of Dimethyl sulfoxide (DMSO). 100 µl of this solution were mixed with 900 µl of Acetonitrile:Methanol (1:1) and used as a positive control.

Cell Culture Growth:
HCT-116 (ATCC CCL-247) or HT-29 (ATCC HT-B38) colon cells, BJ-hTERT fibroblast (ATCC, CRL-4001), HaCaT (keratinocytes) skin cells or MDA-MB-231 breast cancer cells were grown at 37° C. in a humidified 5% $CO_2$, 95% air atmosphere. HCT-116 and HT-29 cells were maintained in McCoy's 5a Medium Modified while BJ-hTERT, HaCaT and MDA-MB-231 cells were cultured in DMEM supplemented with 10% fetal bovine serum (FBS).

Determination of Anti-Inflammatory Activity

Excitation and Treatment of Cells:
Cells were seeded in 24-well plates at 50,000 cells per well in triplicate in 500 µl of the appropriate culture medium. The cells were incubated for 24 h at 37° C. in a humidified 5% $CO_2$-95% air atmosphere. Unless stated differently, cells were treated with a 1:10 dilution of plant extracts.

For analyzing the formulated creams prepared for *Erodium* water extracts, 250 mg of each cream were diluted in 750 µl water. 50 µl of the prepared solution (~1:12 dilution) was added per well in order to test for anti-inflammatory activity.

For analyzing the anti-pollutant effect of *Erodium* water extracts, UVC or $H_2O_2$ treated cells were prepared.

TNF-α Activation (TNF-α):
cultures in each well were treated with 50 ng/ml recombinant human TNF-α (Peprotech, Cat. #300-01A) and 50 µl (1:10 dilution) of plant extract as described above. Since the culture cells used are known to produce baseline level of interleukin 8 (IL-8) in the absence of TNF-α, three different controls were included in all experiments: (a) wells without TNF-α and without plant extracts, (b) wells in which only TNF-α was added, (c) wells with both TNF-α and the relevant solvent. In addition, extracts of *Curcuma longa* and *Curcubita pepo* (Pumpkin) were added to wells containing TNF-α to serve as positive and negative controls, respectively. Cultures were then incubated again at the same conditions for 16 h before IL-8 level were determined.
Lipopolysaccharide (LPS) Excitation:

LPS powder (Sigma, Cat. # L8274) was dissolved in water at a concentration of 1 mg/ml. Then, 75 µl of this working solution were added to each well resulting in a final concentration of 150 ng/ml. Volume adjustment was performed for all wells.

UVC Treatment:

24-well plates were placed open on an elevated stage (19.5 cm elevation) inside the laminar hood. Cells (both treated or not treated with *Erodium* water extract) were exposed to UVC for 60 or 120 minutes.

$H_2O_2$ Treatment:

$H_2O_2$ was added to treated or untreated *Erodium* water extract. The final concentration of was 3.2 mM.

Determination of IL Levels Produced by Cells

IL-8 levels was determined by the DuoSet® ELISA kit (Human CXCL8/IL-8, Cat # DY208-05) according to manufacturer's protocol (R&D Systems). Using a seven point standard curve, the levels of IL-8 (pg/ml) in each well were calculated. For specific activity calculations, the values obtained in wells with plant extracts were subtracted from the values received in the wells containing the control solvent. The net values were then divided by the relevant dry weight of each sample in order to obtain specific activity. Means of replicates were subjected to statistical analysis by multiple comparison Tukey-Kramer test ($P \leq 0.05$). Levels of TNF-α (Cat. # DY210-05), IL-6 (Cat. # DY206-05), IL-12 (Cat. # DY1270-05) and IL-27 (Cat. # DY2526-05) were evaluated using similar kits manufactured by R&D Systems.

XTT Viability Assay:

Cells were seeded in 96-well plates at 10,000 cells per well in triplicate in the appropriate cell culture media and incubated for 24 h at 37° C. in a humidified 5% $CO_2$-95% air atmosphere. The following day, the extracts were added to each well. Wells with media but no cells served as controls. Cells were incubated for 16 hours. XTT (2,3,-bis (2-methoxy-4-nitro-5-sulfophenyl)-5-[(phenylamino)-carbonyl]-2H-tetrazolium inner salt) reduction was used to quantify viability according to manufacturer's instruction (BI, Kibbutz Beit-Haemek, Israel). Cells were incubated with XTT reagent for 2 hours at 37° C. in a humidified 5% $CO_2$-95% air atmosphere. Absorbance was recorded by a photometer SPEKTRAFluor Plus (Tecan, Salzburg, Austria) at 490 nm with 650 nm of reference wavelength. Cell survival was estimated from the equation: % cell survival=100×(At−Ac), where At and Ac are the absorbencies (490 nm) of the XTT colorimetric reaction (BI, Kibbutz Beit-Haemek, Israel) in treated and control cultures, respectively, minus non-specific absorption measured at 650 nm. Absorbance of medium alone was also deducted from specific readings.

Preparation of Drug Solutions for ELISA Assays:

Prednisolone (Sigma, P6004-1G) and Indomethacin were used in order to evaluate the anti-inflammatory activity of *Erodium crassifolium* extracts. Prednisolone solution was prepared by dissolving 7.2 mg in 1 ml ETOH (20 mM). 50 µl of this solution were added to each tested well. Due to the instability of this solution, this drug was replaced with 6α-Methylprednisolone, a stable sodium salt of prednisolone. Working solution for this salt was prepared by dissolving 9.93 mg in 1 ml water (20 mM). 50 µl of this solution were added to each tested well. For Indomethacin, a 25 mg pill was dissolved in 1 ml DMSO. Fifty µl of this solution were added to each tested well.

Antioxidants Activity Assays

1. OxiSelect™ Oxygen Radical Antioxidant Capacity (ORAC) Activity Assay (Cat # STA-345-T) was used for in vitro testing. This assay is based on the oxidation of a fluorescent probe by peroxyl radicals by way of a hydrogen atom transfer (HAT) process. Peroxyl radicals are produced by a free radical initiator, which quenches the fluorescent probe over time. Antioxidants present in the assay block the peroxyl radical oxidation of the fluorescent probe until the antioxidant activity in the sample is depleted. The remaining peroxyl radicals destroy the fluorescence of the fluorescent probe. In this assay, both the antioxidant's inhibition time and inhibition percentage of free radical damage is a single value. The sample antioxidant capacity correlates to the fluorescence decay curve, which is represented as the area under the curve (AUC). The AUC is used to quantify the total peroxyl radical antioxidant activity in a sample and is compared to an antioxidant standard curve of the water soluble vitamin E analog Trolox™. The assay was performed according to manufacturer instructions (Cell Biolabs Inc.).

2. Antioxidant activity was also measured using the OxiSelect™ Cellular Antioxidant Assay (Cat # STA-349) manufactured by Cell Biolabs. 60,000 cells per well were cultured in a 96-well black fluorescence cell culture plate until confluent. Then the cells were pre-incubated with a cell-permeable DCFH-DA fluorescence probe dye and the bioflavonoid Quercetin, or the antioxidant sample being tested. After a brief incubation, the cells were washed, and the reaction started by adding the free radical initiator. This reagent creates free radicals that convert the probe to highly fluorescent DCF. Quercetin or the antioxidant sample inhibits the formation of free radicals, and thus DCF formation, in a concentration dependent manner. Fluorescence was measured over time in a standard microplate fluorometer. This fluorescence correlates to the Quercetin's ability to quench free radicals. Test antioxidant values can be compared to Quercetin to determine antioxidant activity within the cell. The assay was performed according to manufacturer instructions.

Quantitative Real-Time Polymerase Chain Reaction (qRT-PCR):

Cells were seeded in 6-well plates at a concentration 1,500,000 cells per well. After a 24 h incubation at 37° C. in a humidified 5% $CO_2$-95% air atmosphere, cells were treated with TNF-α (final concentration of 1 ng/ml) followed by treatment with *Erodium* water extract (Erod15 and Erod30 are 15× and 30× dilutions respectively). Non-treated cells or cells treated only with TNF-α served as negative and positive controls. Cells were then re-incubated for 24 h at 37° C. in a humidified 5% $CO_2$-95% air atmosphere. The next day, cells were harvested and total RNA was extracted using Trizol (Invitrogen, Carlsbad, Calif., USA) according to the manufacturer's protocol. Two micrograms of RNA was reverse-transcribed in a total volume of 20 µl using the High Capacity cDNA kit (Invitrogen). MMP-9 Primers were designed using Primer3Plus software. PCR was performed in triplicate using a Rotor-Gene 6000 (Corbett Life Sciences) and SYBR Green (Invitrogen, Foster City, Calif.) according to the manufacturer's protocol. The expression of each target gene was normalized to the expression of GAPDH mRNA and is presented as the ratio of the target gene to GAPDH RNA, expressed as $2-\Delta Ct$, where Ct is the threshold cycle and ΔCt=Ct Target−Ct GAPDH. Experiments were repeated three times.

Fractionation of *Erodium* Water Extract Through High Performance Liquid Chromatography (HPLC)

Sample Preparation:

The concentrated *Erodium* extract was dissolved in deionized water and filtered through 0.45 um syringe filter. The filtered extract was loaded in HPLC for separation. The concentrated *Erodium* extract was dissolved in deionized water and filtered through 0.45 um syringe filter. The filtered extract was loaded in HPLC for separation. The hydrolyzed extract was treated with 2N HCL in 1:1 proportion and incubated at 80° C. for one hour prior to HPLC run.

HPLC Separation:

The separation of the sample was carried out with Ultimate 3000 HPLC system coupled with WPS-3000(T) Autosampler, HPG-3400 pump, DAD-300 detector. The separation was performed on a Purospher RP-18 endcapped column (250 mm×4.6 mm I.D.; Merck KGaA, Darmstadt, Germany) with a guard column (4 mm×4 mm I.D.). Solvent gradients were formed by varying the proportion of solvent A [water (0.1% acetic acid)] to solvent B (methanol) with the flow rate of 1.0 ml/min. Initially Solvent B was maintained at 10% for 10 min and then subsequently increased to 45% in 25 min. The 45% of Solvent B was maintained for 5 min and then decreased to 10% in 10 minutes and equilibrated for 5 min. The compounds peaks were detected with three different wavelengths—220 nm, 240 nm and 280 nm.

Statistical Analyses:

Results are presented as mean and S.E. of replicate analyses and are either representative of, or inclusive of at least 2 independent experiments. Means of replicates were subjected to statistical analysis by Tukey-Kramer test (P≤0.05) using the JMP statistical package and regarded as being significant when P≤0.05 (*). GraphPad Prism (version 6 for windows, GraphPad software Inc. San Diego, USA) was employed to produce dose-response curve and IC50 doses for *Erodium* extracts by performing nonlinear regression analysis.

Results

*Erodium crassifolium* Extracts have Anti-Inflammatory Activity:

In order to test whether bulbs of *E. crassifolium* comprise anti-inflammatory activity, the effect of tuber extracts on HCT-116 human colon cells which were stimulated with TNF-α were compared to the effect of commercial pills of *Curcuma longa* (positive control) or extracts from *Curcubita pepo* (negative control). As seen in FIGS. 2A-B extracts of *E. crassifolium* reduced the amount of IL-8 secreted by the TNF-α stimulated cells.

In order to identify the *E. crassifolium* extract with the highest activity. HCT-116 human colon cells (FIG. 3A) or BJ-hTERT skin cells (FIG. 3B) were stimulated with TNF-α followed by treatment with *Erodium* extracts. *Curcuma longa* extract from commercial pills served as positive control. *Curcubita pepo* water extract was used as negative control.

As illustrated in FIGS. 3A-B, the highest activity was obtained when extraction was carried out in water as exemplified in both colon and skin cells.

Determination of $IC_{50}$ for *Erodium crassifolium* Extracts:

In order to determine $IC_{50}$ for *E. crassifolium* extracts, XTT assays using different dilutions of the extract were performed in MDA-MB-231, HCT-116 and HaCaT cell lines (FIGS. 4A-C).

In all three types of cells when the non-diluted extract was used, the majority of cells did not survive. However, in all three types a higher dilutions results in higher than 50% survival. According to $IC_{50}$ calculations, $IC_{50}$ values for the different types of cells are as follow: $IC_{50}$ MDA-MB-231=7.428; $IC_{50}$ HCT-116=13.55; $IC_{50}$ HaCaT (KER)=6.132. These calculations imply that each cell type reacts different to treatment with *Erodium* water extract. Also, it was noted that normal cells (HaCaT) are less sensitive than cancerous ones (HCT-116 and MDA-MB231). In all three cases the $IC_{50}$ obtained is higher or similar to than that used for inflammation assays. Since anti-inflammatory assays are performed using an approximately 11.5 fold dilution (50 μl extract in a total volume of 575 μl) the reported anti-inflammatory activity is obtained with extract concentrations below or similar to the $IC_{50}$. Thus, the *E. crassifolium* extracts are safe for use as nutraceuticals or for derma-cosmetic products.

Stability of *Erodium* Water Extracts at in Different Conditions and in Different Tuber Stages:

*Erodium* extracts were prepared without drying and stored at either 4° C. or −20° C. Activity using the IL-8 reduction assay in colon HCT-116 cells was tested for different dilutions (1:20; 1:40; 1:80 and 1:160) prepared for the samples stored at either temperature (FIG. 5). Extracts of *Curcuma longa* (in ACN:MT) and *Cucurbita pepo* (in water) served as positive and negative controls respectively.

The experiment results show that the active compound/s are still active after diluting the extract 1:40 but the activity obtained for additional dilutions (1:80 and 1:160) is lower but not necessarily significantly different.

In another experiment, water *Erodium* extracts were treated as follows: the liquid *Erodium* water extract was divided into 4 equal portions. A sublimation step was carried out in order to dry the sample. After sublimation each portion was stored for 5 days at a different temperature—(−20° C.), 4° C., 20° C. and 37° C. and the activity of each portion was tested by the IL-8 ELISA test on HaCaT skin cells.

As illustrated in FIG. 6, the active compound/s are most stable when stored at (−20° C.). Higher temperatures resulted in less activity. Interestingly, increasing temperatures from 4° C. to 37° C. resulted in higher activity implying that this change in temperature might release or activate the active compound due to some process occurring in the extract. In a second experiment, the same dilutions previously used were prepared and re-tested using the dried extracts stored at (−20° C.) in both HCT-116 (FIG. 7A) and BJ-hTERT (FIG. 7B). In addition, a second extraction cycle, re-using the *Erodium* mush was tested.

The production of anti-inflammatory compounds and their stability was also evaluated in two different tuber stages, S2 and S3. The classification to four different tuber stages depends on the size and color of tubers. The majority of tubers that were isolated from the soil belonged to stages S2 and S3. Since tubers are a storage organ, it is reasonable that the anti-inflammatory substances will be more abundant in these stages rather than in young tuber (S1) or mature ones (S4). Therefore, sublimated *Erodium* water extracts produced from S2 and S3 separately were stored dry or wet (re-suspended in water after sublimation) at (−20° C.), 4° C. and 37° C. for a period for either 2 or 5 weeks. At the end of each time period, stability and activity was tested by the IL-8 ELISA assay carried out on HaCaT (KER) skin cells (FIGS. 8A-B).

As shown in FIGS. 7A-B and 8A-B modifying the extraction process by adding a sublimation step resulted in higher stability of the extracts regardless of whether samples were stored dry or wet. Furthermore, after sublimation, extracts were stable at all temperatures tested regardless to whether storage was in dry or wet conditions.

Anti-Inflammatory Activity is Found in Both Peel and Flesh of *Erodium* Tubers:

In order to determine whether the anti-inflammatory substances are synthesized in the tuber's peel or flesh, water extractions were prepared from both tissues. Anti-inflammatory activity was evaluated by the IL-8 ELISA assay in HaCaT (KER) skin cells.

As illustrated in FIG. 9, anti-inflammatory activity was found in both tuber's peel and flesh.

Anti-Inflammatory Activity was Found in *Erodium* Leaves and Wild Type Strain:

Extracts were prepared from WT *Erodium* tubers (FIG. 10A) of from leaves of cultivates plants (FIG. 10B). Activity was evaluated by the reduction levels of IL-8 in HaCaT (KER) skin cells. As illustrated in FIGS. 10A-B, both leaves of cultivated *Erodium* and WT *Erodium* tubers possessed anti-inflammatory activity.

Comparison of *Erodium* Water Extracts with Prednisolone and NSAID Indomethacin:

As illustrated in FIGS. 11A-B, the highest reduction in IL-8 levels when tested skin cells were obtained with *Erodium* extract. Furthermore, these levels were significantly different from those obtained with either prednisolone, indomethacin or the *Curcuma longa*, the positive control.

*Erodium* Water Extracts Alleviates Inflammation Caused by Lipopolysaccharides (LPS):

Many case of inflammation are triggered by the presence of microorganisms found in the inflamed tissue. These microorganisms either secret different compounds or contains molecules such as lipopolysaccharides that elicit the inflammation process. The cytokine IL-8 is known to be part of the body response to such microorganism invasion. Its expression is induced after a cascade of reactions occurring upon identification of LPS by the body. Several other important molecules, including TNF-α and NF-κB are part of this cascade event. Since TNF-α and IL-8 expression occurs at different time points along the inflammation process it was important to identify their expression peaks in the present system. Therefore, experiment analyzing the timing of expression for both TNF-α and IL-8 and further analyzing whether *Erodium* extracts can alleviate inflammation triggered by LPS were carried out.

TNF-α is located upstream the cascade event and is known to initiate IL-8 expression. TNF-α expression is reported to be short and transient. Although the values obtain for TNF-α are not significantly different the highest expression is observed after a short period (1 hr). On the other hand, IL-8 that is located downstream the cascade, reached the highest values after 24 hr (FIG. 12A). Therefore, the influence of *Erodium* water extract on LPS-triggered inflammation was evaluated 24 hours after LPS-excitation. The results clearly show that this extract alleviates inflammation by reducing IL-8 levels (FIG. 12B).

The Effect of *Erodium* Water Extract on Additional ILs Tested:

The purpose of this set of experiments was to test whether the levels of other inflammation-related cytokines, IL-6, IL-12 and IL-27, are affected when treating the cells with *Erodium* extract (FIGS. 13A-D). The procedures were similar to those applied for IL-8 and similar ELISA kits from the manufacturer were used to detect these ILs. IL-8 assay was used as a control to verify the system was working.

A standard curve (not shown) was obtained for all the ILs tested. IL-6, IL-12, and IL-27 all showed basal OD reads implying that these cytokines were not induced upon TNF-α treatment.

Antioxidant Activity of *Erodium crassifolium* Extracts:

Oxidative stress is a result of an imbalance between reactive oxygen metabolites (ROM) production and neutralizing capacity of antioxidant mechanisms. Oxidative damage of lipids and other macromolecules such as DNA and RNA results in alteration of cell membranes and other cellular components. Evidence is accumulating that oxidative stress is involved in many pathological processes, including: rheumatoid arthritis, asthma, cancer, macular degeneration, inflammatory Bowel Disease (IBD), neurodegenerative diseases such as Parkinson's and Alzheimer diseases, arthritis, diabetes mellitus, atherosclerosis and chronic fatigue syndrome.

The antioxidant assays reveal a high antioxidant activity derived from *Erodium* water extracts (FIGS. 14A-D). Furthermore, this activity was shown to be higher than that found in green and black teas that are known for their antioxidant activity. The combination of both anti-inflammation and antioxidant activities in the same *Erodium* extract is of great importance for development of future products based on this plant extracts.

Anti-UV and Hydrogen Peroxide Induced Inflammation Activity of *Erodium crassifolium* Extracts:

In the last two decades the effect of polluted air or water on human diseases is of high interest. The skin, as the body's main barrier is a target organ for pollution and also the site of significant absorption of environmental pollutants. Some diseases such as allergies and cancer are affected by pollutants such as UV radiation, hydrogen peroxide (or other ROS generators) and arsenic molecules in water and crops.

The anti-pollutant activity of *Erodium* water extracts was tested in HaCaT (KER) skin cells. These cells were UVC-treated or exposed to $H_2O_2$ in the presence or absence of *Erodium* water extracts. The anti-pollutant activity was determined by the IL-8 ELISA assay described previously. As shown in FIGS. 15A-B, HaCaT (KER) skin cells exposed to either UVC or hydrogen peroxide ($H_2O_2$) in the presence of *Erodium* water extracts revealed lower level of IL-8 compared to the untreated control cells. These results suggest that *Erodium* water extracts protect the cells also from pollutants as UVC and $H_2O_2$. The combination of anti-inflammation, antioxidant and anti-pollutant activities in the same *Erodium* extract is of great importance and makes this extract a powerful candidate for development of future products food supplements, cosmetic, derma-cosmetic and skin beauty products based on this plant.

Treatment with *Erodium* Water Extracts Reduces Expression of Matrix Metalloproteinase-9 (MMP-9):

MMP-9, a member of the matrix metalloproteinase family that degrades collagen IV and processes chemokines and cytokines, participates in epidermal remodeling in response to stress and injury. Limited activity of MMP-9 is essential while excessive activity is deleterious to the healing process. Tumor necrosis factor (TNF-α), a key mediator of cutaneous inflammation, is a powerful inducer of MMP-9. In order to evaluate whether *Erodium* water extracts effected expression of MMP-9, mRNA was purified from TNF-α-stimulated HaCaT cells in the presence and absence of *Erodium* water extracts. The expression of MMP-9 was normalized to the expression of GAPDH mRNA and measured by q-RT-PCR.

As illustrated in FIG. 16, treatment of HaCaT (KER) skin cells with *Erodium* water extract at both concentrations used, reduced the expression levels of MMP-9 mRNA.

Chemical Characterization of *Erodium crassifolium* Extract:

*Erodium crassifolium* water extract was subjected to HPLC fractionation as described in material and methods.

Retention time and area of the peaks detected from HPLC chromatogram illustrated in FIG. 17 of *Erodium* water extract are summarized in Table 1 below. Asterisk indicates the major peaks showing biological activity (anti-inflammatory activity) as detected by IL-8 ELISA assay.

TABLE 1

| Sample No. | Ret. Time Min | Area mAU*min (220 nm) | Area mAU*min (240 nm) | Area mAU*min (280 nm) | Fractions |
|---|---|---|---|---|---|
| 1 | 2.74 | 103.742 | 16.722 | 4.511 | Fraction 1 |
| 2 | 3.45 | 122.537 | 23.163 | 1.071 | Fraction 2 |
| 3 | 3.75 | — | 0.224 | 1.185 | |
| 4 | 4.19 | 30.589 | 0.92 | 0.989 | |
| 5 | 4.85 | 15.445 | 0.585 | 3.752 | |
| 6 | 5.12 | 2.454 | 0.407 | — | |
| 7 | 5.79 | 5.283 | 1.024 | 1.49 | |
| 8 | 6.23 | 2.546 | 0.692 | — | Fraction 3 |
| 9 | 6.61 | 18.282 | 2.138 | 6.061 | |
| 10 | 8.45 | 1.85 | 3.413 | 0.183 | |
| 11* | 10.11 | 60.664 | 18.669 | 2.522 | Fraction 4 |
| 12* | 13.66 | 56.35 | 2.864 | 9.961 | Fraction 5 |
| 13 | 16.71 | 16.643 | 5.014 | — | Fraction 6 |
| 14 | 18.2 | 5.27 | 1.389 | 0.605 | Fraction 7 |
| 15 | 19.02 | 2.682 | 0.874 | 0.197 | |
| 16 | 20.4 | 5.276 | 1.768 | — | |
| 17* | 20.84 | 33.37 | 9.047 | 6.955 | Fraction 8 |
| 18 | 22.39 | 2.5 | 0.547 | 1.696 | |
| 19 | 23.05 | 8.683 | 2.192 | 1.22 | |
| 20 | 25.47 | 3.274 | 0.858 | 0.321 | Fraction 9 |
| 21* | 26.52 | 40.509 | 9.635 | 8.86 | |
| 22 | 36.05 | — | 1.61 | 0.74 | Fraction 13 |

As shown in Table 1, 13 fractions were obtained that revealed 23 peaks. The amount of IL-8 was analyzed in each peak by ELISA (FIG. 17).

The retention time and area of the peaks detected from HPLC chromatogram of non-hydrolyzed *Erodium* water extract vs. the hydrolyzed one at 240 nm is summarized in Table 2, herein below.

TABLE 2

| Sample No. | Ret. Time Min | *Erodium* (normal) Area mAU*min (240 nm) | *Erodium* (hydrolyzed) Area mAU*min (240 nm) |
|---|---|---|---|
| 1 | 2.74 | 16.722 | 175.85 |
| 2 | 3.45 | 23.163 | 29.318 |
| 3 | 3.75 | 0.224 | 18.602 |
| 4 | 4.19 | 0.92 | — |
| 5 | 4.85 | 0.585 | 5.37 |
| 6 | 5.12 | 0.407 | — |
| 7 | 5.79 | 1.024 | 1.73 |
| 8 | 6.23 | 0.692 | 5.24 |
| 9 | 6.61 | 2.138 | 6.62 |
| 10 | 7.79 | — | 0.654 |
| 11 | 8.45 | 3.413 | 4.484 |
| 12* | 10.11 | 18.669 | 106.856 |
| 13 | 13.66 | 2.864 | 0.4 |
| 14 | 16.71 | 5.014 | 14.108 |
| 15 | 18.2 | 1.389 | 1.286 |
| 16 | 19.02 | 0.874 | — |
| 17 | 20.4 | 1.768 | — |
| 18 | 20.84 | 9.047 | — |
| 19 | 22.39 | 0.547 | — |
| 20 | 23.05 | 2.192 | — |
| 21 | 25.47 | 0.858 | — |
| 22 | 26.52 | 9.635 | — |
| 23 | 36.05 | 1.61 | — |
| 24 | 38.43 | 0.393 | — |

As illustrated in FIG. 17, at least 4 fractions (Fractions 4, 5, 8, and 9) harbor biological activity.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating breast cancer in a subject in need thereof comprising administering to the subject a therapeutically effective amount of a polar extract of tubers of an *Erodium crassifolium* L'Her plant, thereby treating the breast cancer.

2. The method of claim 1, wherein the extract has not been boiled for more than 1 minute, 10 minutes or 20 minutes.

3. The method of claim 1, wherein said extract does not comprise a plant tissue.

4. The method of claim 1, wherein the extract is an aqueous extract.

* * * * *

UNITED STATES PATENT AND TRADEMARK OFFICE
CERTIFICATE OF CORRECTION

PATENT NO. : 10,960,035 B2  
APPLICATION NO. : 15/563595  
DATED : March 30, 2021  
INVENTOR(S) : Hinanit Koltai et al.

Page 1 of 1

It is certified that error appears in the above-identified patent and that said Letters Patent is hereby corrected as shown below:

On the Title Page

Item (73) Assignees, Line 4:  
"(ARO) (Voleaui Center)" should be changed to --(ARO) (Volcani Center)--  
Also, at Line 5:  
"Rishon-LeZiou" should be changed to --Rishon-LeZion--

Signed and Sealed this  
Fourteenth Day of December, 2021

Drew Hirshfeld  
*Performing the Functions and Duties of the*  
*Under Secretary of Commerce for Intellectual Property and*  
*Director of the United States Patent and Trademark Office*